United States Patent [19]

Block

[11] Patent Number: 6,043,092

[45] Date of Patent: Mar. 28, 2000

[54] CELL CULTURE MEDIA FOR MAMMALIAN CELLS

[75] Inventor: Geoffrey D. Block, Pittsburgh, Pa.

[73] Assignee: University of Pittsburgh, Pittsburgh, Pa.

[21] Appl. No.: 08/617,325

[22] Filed: Mar. 18, 1996

[51] Int. Cl.[7] ................................ C12N 5/00; C12N 5/02
[52] U.S. Cl. .................... 435/405; 435/325; 435/366; 435/370; 435/383; 435/384; 435/387; 435/388; 435/389; 435/404; 435/406; 435/407
[58] Field of Search ..................................... 435/325, 366, 435/370, 383, 384, 387, 388, 389, 404, 405, 406, 407

[56] References Cited

U.S. PATENT DOCUMENTS

| | | | |
|---|---|---|---|
| 5,342,777 | 8/1994 | Cole et al. ................................ | 435/378 |
| 5,380,660 | 1/1995 | Jefferson et al. ........................ | 435/404 |
| 5,468,635 | 11/1995 | Komiya et al. ........................... | 435/404 |
| 5,529,920 | 6/1996 | Cole et al. ................................. | 435/6 |
| 5,559,022 | 9/1996 | Naughton et al. ....................... | 435/370 |
| 5,576,207 | 11/1996 | Reid et al. ............................... | 435/378 |

OTHER PUBLICATIONS

Mitaka et al. Hepatol. vol. 16 (2), pp. 440–447, 1992.
Mitaka et al. Hepatol. vol. 13 (1), pp. 21–30, 1991.
Mitaka et al. J. Cell Physiol. vol. 157, pp. 461–468, 1993.
Mitaka et al. Cancer Res. vol. 53, pp. 3145–3148, 1993.

*Primary Examiner*—Leon B. Lankford, Jr.
*Assistant Examiner*—Christopher R. Tate
*Attorney, Agent, or Firm*—Alston & Bird LLP

[57] ABSTRACT

A chemically defined mammalian cell culture medium is provided that supports maintenance and long term clonal growth of mammalian hepatocytes and other cells.

19 Claims, 11 Drawing Sheets

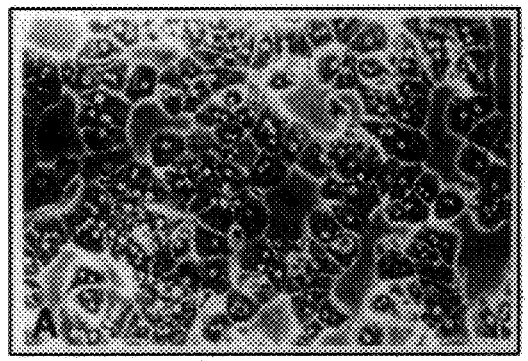
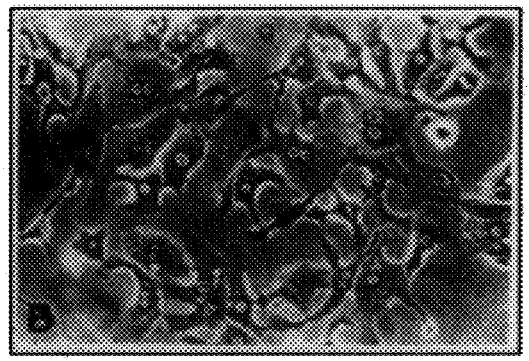
Fig. 4A          Fig. 4B
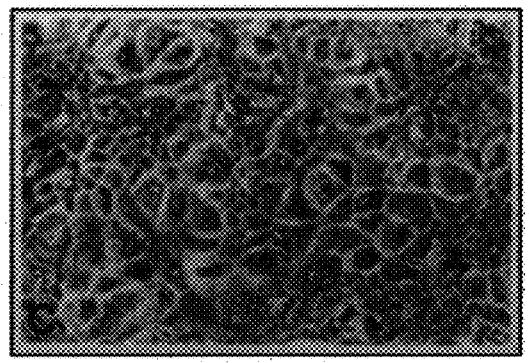
Fig. 4C
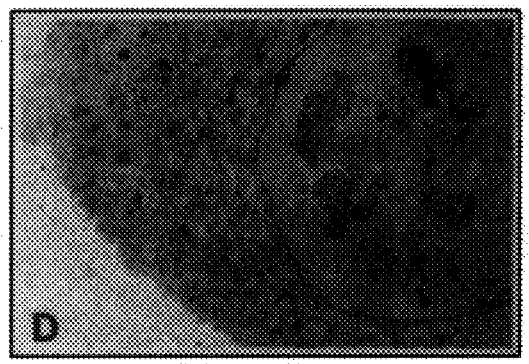
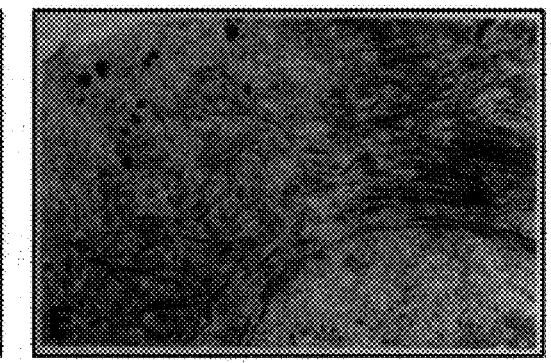
Fig. 4D          Fig. 4E
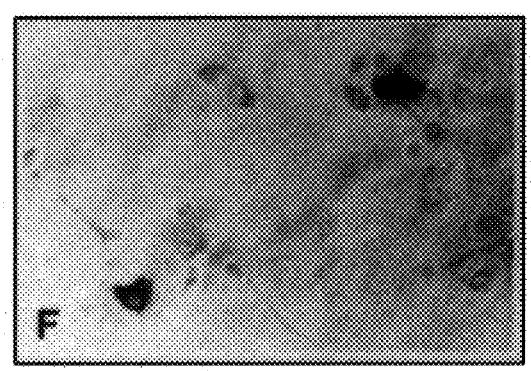
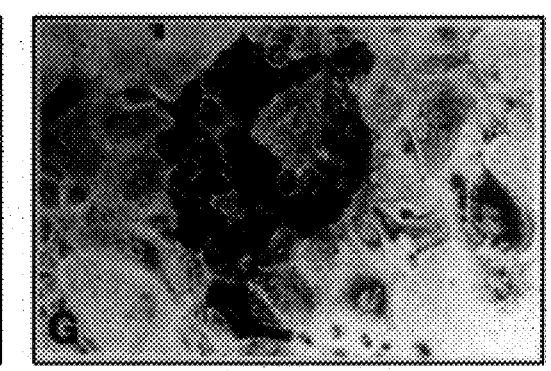
Fig. 4F          Fig. 4G

CELL CULTURE MEDIA FOR MAMMALIAN CELLS

FIELD OF THE INVENTION

The present invention relates generally to cell culture media for mammalian cells. In particular, the invention relates to cell culture media that allow long-term expansion and maintenance of a cell population of mammalian hepatocytes, hepatocyte-derived cell lines, hepatocyte-derived malignant cells, and other cells.

BACKGROUND OF THE INVENTION

It is well-known that specific cell lines can be grown in vitro in optimally formulated culture or nutrient media. Examples of some of the culture media developed for special purposes are: RPMI Media 1640 medium for growth of human B-lymphoid cells and malignant cells, Changs medium for growth of amniotic fluid cells, Medium 199 for growth of mouse fibroblast cells, Minimal Essential Medium (MEM) medium, a "minimal" medium for growth of attached mammalian cells, and Leibovitz medium for growth in absence of $CO_2$. Such various media are distinguished from one another in that they contain critically different components in precise amino acids, vitamins, organic salts, trace elements, and other organic compounds which promote the maximum growth of the cultured cells.

For the growth of mammalian cells chemically defined media are usually supplemented with various sera, preferably fetal calf or newborn calf serum, and other incompletely defined growth factors. A major drawback to serum, however, is that its constituents may vary widely, thereby introducing undefined biological components into the nutrient medium which contributes to the variability of biochemical and cellular events. Additionally, serum is expensive and may result in critical immune reactions in patients if the cells are used for clinical purposes.

The present invention is primarily directed to culturing mammalian hepatocyte cells using chemically defined media that allow long-term expansion of the cell population. The term "chemically defined media" is used in tissue culture to refer to culture media of known chemical composition, both quantitatively and qualitatively, as contrasted with media which contain natural products such as animal serum.

Liver regeneration is achieved primarily by cell division of mature adult hepatocytes as reported by Grisham, J. W., et al., *Cancer Res.* 22:842 (1962), the disclosure of which is incorporated herein by reference. These cells, or a fraction thereof, have a high capacity for clonal growth, as shown by hepatocyte transplantation experiments in ectopic sites (Jirtle, R. L., et al., *Cancer Res.* 42:3000 (1982), the disclosure of which is incorporated herein by reference) and in transgenic mouse models (Rhim, J. A., et al., *Science* 263:1149 (1994), the disclosure of which is incorporated herein by reference). It has been shown in several studies, however, that when liver is stimulated to regenerate while proliferation of mature hepatocytes is suppressed, faculative stem cells emerge and proliferate. See, for example, Thorgeirsson, S. S., et al., *Proc. Soc. Exp. Biol. Med.* 204:253 (1993), the disclosure of which is incorporated herein by reference. Such cells, sometimes referred to as "oval cells," can mature into hepatocytes in defined animal models or ductular structures composed of cells ("ductular hepatocytes") with mixed hepatocyte and bile duct epithelial markers. See, Gerber, M. A., et al., *Amer. J. Path.* 110:70 (1983) and Vandersteenhoven, A. M., et al., *Arch. Pathol. Lab. Med.* 114:403 (1991), the disclosures of which are incorporated herein by reference. Little is known, however, about their origin and about the controls that regulate their phenotypic transitions to hepatocytes or ductular cells.

Despite the high capacity of hepatocytes to proliferate in vivo, directly or via faculative stem cell growth, the conditions that determine their growth potential and their phenotypic transitions are not thoroughly understood because of only limited success in hepatocyte growth in primary culture. It is typically the case that hepatocytes in primary culture under the influence of primary mitogens enter into one or two divisions and then the cells degenerate and die. Heretofore various investigators have failed to develop a medium that allows hepatocytes to both proliferate and survive.

For example, Berry, N. M., et al., *J. Cell. Biol.* 43:506 (1969), the disclosure of which is incorporated herein by reference, taught the collagenase perfusion technique which allows liver tissue to dissociate into its component cellular elements, based on size. Later, Bissell, D. M., et al., *J. Cell. Biol.* 59(3):722 (1973) and Bonney, R. J., et al., *In Vitro* 9:399 (1974), the disclosures of which are incorporated herein by reference, described the first methods for culturing isolated hepatocytes which perhaps survived for one or two days. Long term culture of hepatocytes on collagen gels for a maximum of 7 to 10 days was reported by Michalopoulos, G., et al., *Exp. Cell. Res.* 94(1):70 (1975), the disclosure of which is incorporated herein by reference. The common characteristic of all of the above-referenced systems is that the hepatocytes in those systems were maintained in culture without there being any evidence of cell proliferation. These systems were, instead, only maintenance cultures of non-proliferating cells for a brief period.

The first successful attempt to initiate DNA synthesis in hepatocytes used the then newly-discovered epidermal growth factor (EGF) as reported by Richman, R. A., et al., *Proc. Nat. Acad. Sci. USA* 73:3589 (1976), the disclosure of which is incorporated herein by reference. Over the ensuing years several other groups of researchers used EGF as a mitogen for hepatocytes and reported on the mitogenic effects of EGF and their modulation by other factors such as, for example, matrices such as collagen Type I, zinc, and proline.

Hepatocyte growth factor, also known as scatter factor (hereinafter referred to as "HGF" or "HGF/SF") was discovered, cloned and ultimately sequenced by the late 1980's. See Michalopoulos, G., et al., *Federation Proceedings* 42:1023 (1983); Michalopoulos, G., et al., *AACR Proceedings* 24:58 (1983); Michalopoulos, G., et al., *Cancer Res.* 44(10):4414 (1984); and Miyazawa, K., et al., *Biochem. Biophys. Res. Comun.* 163:967 (1989), the disclosures of which are incorporated herein by reference. HGF/SF was found to be a mitogen for many hepatocytes as well as for epithelial cells. HGF/SF's importance for the liver is due to the fact that it is the trigger for liver regeneration through an endocrine mechanism.

Recently, several studies have shown that HGF/SF, epidermal growth factor ("EGF"), and transforming growth factor α ("TGFα") are the primary mitogens for hepatocytes in culture by stimulating limited hepatocyte DNA synthesis in chemically defined media. See, for example, Michalopoulos, G. K., *Fed. Am. Soc. Exp. Biochem J.* 4:176 (1990), the disclosure of which is incorporated herein by reference. These growth factors were later found to additionally play a role in vivo in liver regeneration after partial hepatectomy. Injection of HGF/SF, TGFα, or EGF in rats induces DNA synthesis in hepatocytes. See, for example, Liu, M. L., et al., *Hepatology* 19:1521 (1994), the disclosure of which is incorporated herein by reference.

In all of these systems, however, it was reported that hepatocytes entered into DNA synthesis and mitosis for only a limited time, typically 1–3 days. After 1–2 rounds of DNA synthesis and cell division, the cultures degenerated and all the cells were dead in about 7–10 days. Until now, there has also been no documented expansion of the number of hepatocytes in cell culture by adding either EGF or HGF alone, or in combination. The cell replication in cultures containing these growth factors is instead self-limited and the number of hepatocytes that die exceeds the number of hepatocytes that are newly generated. The cell replication in cultures containing other hepatocyte mitogens such as transforming growth factors, such as TGFα, and acidic fibroblast growth factor is similarly self-limited.

More recently, Mitaka, T., et al., *Hepatology* 13(1):21 (1991); Mitaka, T., et al., *Hematology* 16(2):440 (1992); Mitaka, T., et al., *Virchows Arch. B Cell Pathol. Incl. Mol. Pathol.* 62:329 (1992); and Mitaka, T., et al., *Cancer Res.* 53:3145 (1993), the disclosures of which have been incorporated herein by reference, have reported that adding nicotinamide, dexamethasone and EGF to a conventional culture medium resulted in the formation of colonies of small hepatocytes arising in a dense culture of standard size parenchymal hepatocytes. In a further study, Mitaka, T., et al., *J. Cell. Physiol.* 157:461 (1993), the disclosure of which is incorporated herein by reference, have reported that the numbers of colonies induced by the combinations of EGF+ HGF, EGF+TGF-α, and HGF+TGF-α were not different from those of colonies induced by each mitogen alone. In these studies, however, there was no significant expansion of the total cell population, no evidence of clonal growth, and there was loss of differentiation.

Until now there has been no chemically defined medium, supplemented or not, which is able to support long term proliferation, differentiation, and viability of hepatocytes. While for many purposes the use of an undefined supplement is satisfactory, in cases where studies are made of growth, metabolism, and/or differentiation of cells in culture, it is most desirable to have a supplement that is defined. The introduction of undefined components to a cell culture can contribute to variability, unpredictability, and contamination in study results and applications of cell cultures. The use of defined media is particularly important and advantageous in areas of drug metabolism, artificial organ development, cell transplantation, gene therapy, and basic investigational cell studies.

The above-described limited capacity of hepatocytes to proliferate in primary culture has hindered long-term studies or uses that required long-term viability or proliferation. Applications of hepatocyte cultures to cellular transplantation and gene therapy have thus been hindered. Consequently, there remains a need for a chemically defined medium that will allow hepatocytes to proliferate and survive long term. Among the potential applications for such a medium and the hepatocytes and other cells so cultured are gene therapy, bioartificial organs, cell transplants, drug production, and drug and chemical testing.

As stated above, the current state of the art does not provide a hepatocyte culture system in which hepatocytes expand as a cell population by sustained proliferation, and there is a need for such a system. The present invention provides a fully defined culture medium which allows sustained proliferation and long-term expansion of hepatocytes.

SUMMARY OF THE INVENTION

According to the present invention, a new chemically defined cell culture medium is provided. This medium supports sustained clonal growth of primary hepatocytes and hepatocyte cell lines, genetically transformed hepatocytes, and hepatocytes obtained from neoplastic sources, resulting in expansion of the cell population. This medium further allows complete differentiation of metabolic, structural, and secretory functions of the cells grown therein. Under these conditions, hepatocytes undergo multiple proliferative cycles. Once confluency is reached, or in the presence of specific matrix components, nutrients, and/or growth factors, these proliferating cells stop dividing and maintain a mature hepatocyte phenotype for many months or longer.

Accordingly it is a primary object of the present invention to provide a culture medium for sustained proliferation and viability of hepatocytes.

Another object of the present invention to provide a culture medium for sustained differentiation and viability of hepatocytes.

Yet another object of the present invention is to provide a culture medium for sustained proliferation of hepatocytes that revert to complete differentiation as growth ceases.

Another object of the present invention is to provide a culture medium for long-term expansion of hepatocytes that contains no serum such that the medium is fully defined.

Yet another object of the present invention is to provide a culture medium for sustained proliferation, differentiation, and viability of hepatocytes on a variety of matrix substrates.

These and other objects of the present invention are achieved by one or more of the following embodiments.

In one aspect, the invention features a chemically defined HBM culture medium for maintenance, differentiation, and long-term growth of mammalian hepatocytes, comprising:

(a) a synthetic stock basal medium designed for mammalian cell culture; and (b) a hepatocyte cell growth promoting amount of components selected from among nicotinamide, amino acids, transferrin, hormones, dexamethasone, trace metals, and simple carbohydrate selected from the group consisting of D-glucose and D-galactose and any combination thereof.

In a preferred embodiment the invention features HBM culture medium further comprising buffer, antibiotics, and albumin.

In another aspect, the invention features a mammalian cell culture medium comprising the composition of HGM as defined in Tables I and II, wherein the stock basal media of Table I comprises a blended DMEM such that the final concentration of D-glucose is preferably about 2.0 g/L and the amount of D-galactose is preferably about 2.0 g/L.

Other features and advantages of the invention will be apparent from the following description of the preferred embodiment, and from the claims.

BRIEF DESCRIPTION OF THE DRAWINGS

FIG. 1A shows the percent labeled nuclei (BRdU) of proliferating cell cultures at different times after hepatocyte isolation. The cells were grown in HBM supplemented with HGF/SF and EGF.

FIG. 1B shows the incorporation of [$^3$H] thymidine (disintegrations per minute) into DNA in cultures at different times after hepatocyte isolation. Cells were exposed to HGF/SF in HBM (◇); EGF in HBM (○); HGF/SF+EGF in HBM (Δ); and a control, HBM alone (□).

FIG. 1C shows the amount of DNA per plate at different days of cells grown in HBM medium alone (control) (■); HGF/SF in HBM (Δ); EGF in HBM (▽); and HGF/SF+EGF in HBM (●).

FIGS. 4A–4G are photographs of rat hepatocytes cultured in HBM as described herein under various conditions.

FIG. 4A shows hepatocytes in HBM medium with HGF/SF and EGF at day 1 after isolation showing typical subconfluent non-proliferating hepatocytes.

FIG. 4B shows hepatocytes at day 4 in HBM media induced with HGF/SF showing typical scattered morphology.

FIG. 4C shows hepatocyte cultures having reached confluency at day 15 showing typical morphology.

FIGS. 4D and 4E are election photomicrographs of the cells in FIGS. 4A and 4C, respectively.

FIGS. 4F and 4G are photomicrographs of stained hepatocytes that were transfected at day 3 with a lac-Z-containing replication defective retrovirus and stained for β-galactosidase expression as described below and then photographed at day 1 (FIG. 4F) and day 10 (FIG. 4G) after transfection. The cells were cultured in HBM medium supplemented with HGF/SF and EGF as described below.

FIG. 6A is a phase contrast photomicrograph of cultures of proliferating hepatocytes overlaid with Matrigel at day 8 and photographed at day 18. The granular cytoplasm and the appearance of typical bile canaliculi appear as bright lines between cells.

FIGS. 6B and 6C are low and high power electron photomicrographs, respectively, of cells at day 18 in culture, 10 days after overlay with Matrigel. Typical features of hepatocyte cytoplasm are shown such as lamellae of endoplasmic reticulum wrapping around mitochondria, microbodies with crystalline center, bile canaliculi ("c") (FIG. 6B), abundant mitochondria ("M"), and glycogen ("G") (both in FIG. 6C).

FIG. 6D is a photograph of a Northern blot showing increased expression of albumin mRNA after addition of Matrigel. Albumin mRNA is expressed in control cultures, immediately after isolation from liver by collagenase perfusion and before culture. Expression is minimal at day 8 in culture. At days 3 and 7 after Matrigel addition (lanes marked with "+"), there was an increase in expression of albumin mRNA. GADPH expression was used as an internal control.

FIG. 6E is a photograph of a Northern blot showing induction of cytochrome IIB1 mRNA in cultures treated with Matrigel at day 8 and exposed to phenobarbitol ("PB") 2 days later (day 10 of culture). Cells were harvested at day 15 of culture. GAPDH expression was used as an internal control for mRNA loading.

FIG. 6F is a photograph of a Northern blot of cells cultured additionally with Matrigel (added at day 8 in culture). Cytokeratin 19, a bile duct marker expressed by the proliferating hepatocytes, is suppressed by addition of Matrigel and is not suppressed in control cultures not receiving Matrigel. 28S rRNA stained by ethidium bromide was used as an internal control.

FIG. 7A is a phase contrast photomicrograph (100×) showing the appearance of the ductular structures surrounded by collagen fibrils.

FIG. 7B is a photomicrograph (100×) of parrafin sections of the FIG. 7A type I collagen gels stained with hematoxylin and eosin.

FIGS. 7C and 7D are electron micrographs of cells surrounding the same lumen but in different locations around the lumen of one of the ductular structures seen in FIG. 7B. FIG. 7C shows cells with a morphology similar to bile duct epithelium, with long parallel contacts joined by many desmosomes and with abundant keratin intermediate filaments. FIG. 7D shows cells resembling more of the hepatocyte phenotype, with rough endoplasmic reticulum and mitochondria, densely stained secondary lysosomes and fewer filaments.

FIG. 7E is a photograph of a Northern blot showing that expression of cytokeratins 18 and 19 increases in cultures with ductular/acinar structures whereas albumin is only slightly expressed.

DETAILED DESCRIPTION OF THE INVENTION

Figure 1A:
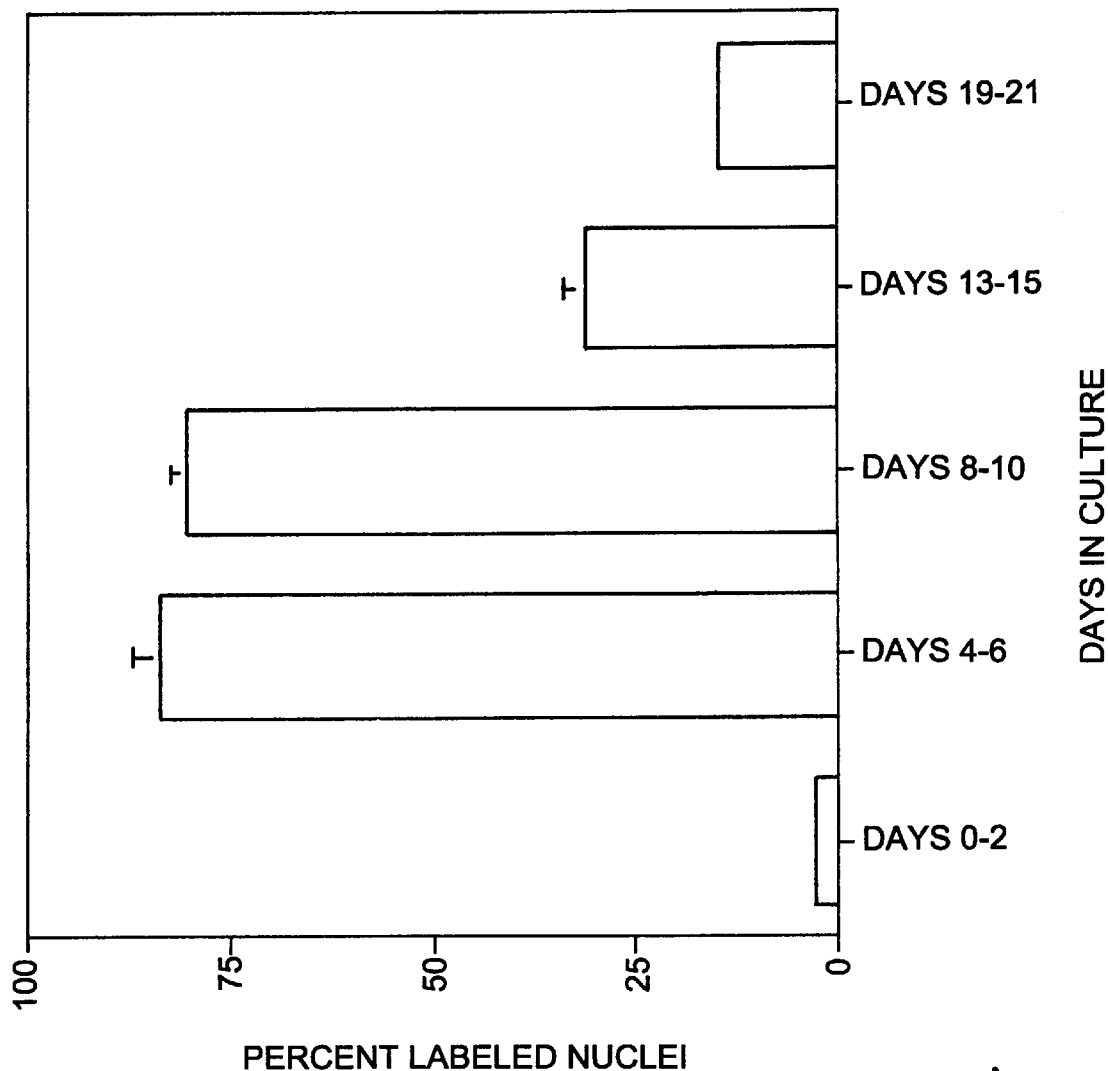
FIGS. 1A–1C are graphs showing results of studies in which rat hepatocytes were cultured in HBM medium as described herein supplemented with growth factors, as indicated. All points represent the mean and standard error of at least three separate cultures.

The present invention provides a hepatocyte basal medium, designated HBM herein, which allows long-term expansion, differentiation and survival of the cell population of hepatocytes, hepatocyte-derived cell lines such as HepG2, hepatic fetal epithelial cells, and hepatic primary hepatocarcinoma cells in vitro. Additionally, the media of the present invention can be used for culturing pancreatic islet cells, renal tubular cells, Ito cells, small intestine epithelial cells, and a variety of cell lines, including MRC5, CaCo, and 3T3 cells, as well as others. The HBM of the present invention maintains metabolic pathways and synthesis functions, i.e., differentiation of mature adult hepatocytes. Additionally, the HBM of the present invention, when combined with specific mitogens and extracellular matrix compositions, hepatocytes can be driven to transdifferentiate into bile duct-like structures. The HBM of the present invention can be used for culture of mammalian hepatocytes, and other cells, including, but not limited to those of human, rat, dog, pig, mouse, and baboon origin.

The HBM medium comprises appropriate levels of essential and non-essential amino acids and bulk ions and trace elements, buffers, vitamins, carbohydrates, lipids, proteins, and hormones to function as a nutrient medium for in vitro mammalian cell culture.

In its broadest aspect the invention features a chemically defined basal media, HBM, that by itself allows for long-term survival, differentiation, and growth of mammalian hepatocytes and other cells. Additionally, in the presence of growth factors such as HGF/SF, EGF, or TGFα, as well as other mitogens, cells growing in the supplemented HBM have a more rapid population expansion and clonal growth. As further demonstrated below, the HBM of the present invention when supplemented with HGF/SF causes formation of bile duct-like structures in conjunction with certain matrix constructs. As stated above, however, such growth factors are not required for specific differentiation patterns in primary cultures, but do accelerate growth and population expansion if this is desired for a specific purpose.

The HBM medium of the present invention comprises a chemically defined stock basal medium (hereinafter referred to as "SM") designed for mammalian cell culture. The stock basal medium can be preferably constructed using Dulbecco's Modified Eagle Medium ("DMEM") as one ingredient, but the present invention is not to be so limited as long as the formulations are within the guidelines set forth herein. Examples of other defined basal medias which may be used in accordance with the present invention include, but are not limited to: Basal Media Eagle (BME), DMEM/F-12 (1:1 DMEM and F-12 vol:vol); Medium 199; F-12 (Ham) Nutrient Mixture; F-10 (Ham) Nutrient Mixture; Minimal Essential Media (MEM), Williams' Media E; and RPMI 1640, all of which are available from Gibco—BRL/Life Technologies, Inc., Gaithersburg, Md., among others. Several versions of many of these media are available, and those that are particularly useful to construct HBM include, but are not limited to: DMEM 11966, DMEM 10314, MEM 11095, Williams' Media E 12251, Ham F12 11059, MEM-alpha 12561, and Medium-199 11151 (all available from Gibco-BRL/Life Technologies (1995–1996 catalog)). Therefore, for example, if L-arginine and/or D-glucose are already in the stock basal media in the necessary amounts, then little or no additional ingredient will have to be added as a supplement.

Depending on the particular composition of the stock basal medium, the SM is then supplemented, as described more fully herein, with D-glucose and/or D-galactose, nicotinamide, other micronutrients comprising amino acids and trace metals not already present in the SM such as L-proline, L-glutamine, L-arginine, L-ornithine, zinc, manganese, copper, and selenium, purified transferrin to which is bound elemental iron or apo-transferrin in combination with iron gluconate, hormones such as dexamethasone and insulin and a pH buffer such as HEPES (N-[2-hydroxyethyl]piperazine-N-[2-ethanesulfonic acid]). Antibiotics such as penicillin and streptomycin, a pH indicator, albumin and/or dextran, essential fatty acids, alternative buffers, vitamins, osmotic agents, and other forms of trace metals may also be optionally added. Typically, a basal medium will have a pH in the range of 6.5–8.2, preferably 7.0–7.7, and most preferably 7.2–7.5.

Phenol red is a typical indicator added to aid in the control of pH. The SM and supplements thereto comprise the HBM medium of the present invention.

The HBM medium may then be optionally supplemented with one or more growth factors such as, for example, HGF/SF, EGF and TGFα if accelerated growth is desired.

Simple carbohydrates D-glucose and/or D-galactose are added to the stock basal media to comprise HBM. If both D-glucose and D-galactose are used, the sum of their total concentrations is preferably 8.0 g/L or less but greater than 0.01 g/L, taking into account the amount of D-glucose present in the stock basal media, if any. When only one of D-glucose or D-galactose is used, the concentration is preferably 5.0–0.1 g/L. For example, in the Example herein, the blended DMEM stock basal medium that was used contained 2.0 g/L D-glucose and no further D-glucose was added. 2.0 g/L of D-galactose was then added as a supplement.

Nicotinamide, another HBM component, has been shown to maintain hepatocyte differentiation, enhance expression of cytochrome P450, and prolong hepatocyte survival in conventional culture to 10–14 days. See, Rosenberg, M. R., et al., In Vitro 18:775 (1982) and Inoue, C., et al., Biol. Chem. 264(9):4747 (1989), the disclosures of which are incorporated herein by reference.

Transferrin is an iron binding protein that interacts with a transferrin receptor on the cell membrane. It serves to both chelate and transport iron ions. The transferrin preferably used in the present invention is either holo-transferrin 30% saturated with iron or is completely unsaturated (apo-transferrin) and is combined with iron gluconate.

Dexamethasone, a synthetic corticosteroid, has been shown to enhance EGF-induced DNA synthesis as reported by Sand, T.-F., et al., Acta. Endocrinol. 109:369 (1985), the disclosure of which is incorporated herein by reference. As used in the present invention, dexamethasone can be any cortisol derivative such as, prednisone, prednisilone, cortisol, hydrocortisone, and other derivatives.

Insulin and insulin-like growth factors are required for glucose uptake, amino acid transport, and maintenance of multiple intermediary metabolic pathways. These effects help to maintain differentiation and support proliferation.

The inclusion of L-arginine in HBM, in the stock basal medium, or supplemental thereto, appears to be important because hepatocytes in culture tend to lose their capacity to synthesize arginine through the urea cycle. In the absence of L-arginine, hepatocytes in culture cannot live for very long because they become incapable of synthesizing L-arginine, thereby blocking their protein synthesis. The use of D-galactose in addition to D-glucose is advantageous for HBM because the combination gives the greatest growth potential over either substance alone.

HGF/SF, EGF, and TGFα, as discussed above, are mitogens which as shown below exhibit an enhanced proliferative effect when used together or alone in accordance with the present invention. The foregoing list of mitogens that can be used to supplement the HBM of the present invention is not exhaustive. It is to be noted, however, that these mitogens are not required for survival or differentiation of hepatocytes when grown in HBM. Hepatocytes grown in HBM will proliferate at a slower rate than if mitogens are added.

The insulin, EGF, HGF, and TGFα used in the presently claimed media can either be recombinantly produced, genetically engineered, or purified from natural sources. The species can be, for example, human, bovine, equine, murine, porcine, or rat.

Several preferred stock basal media—DMEM 11966, DMEM 10314, MEM 11095, and Williams' Medium E 12251 contain the following components per 1000 ml of sterile deionized water as shown below in Table I:

TABLE I

Compositions of Stock Basal Media (mg/L)

| COMPONENT | DMEM 11966 | DMEM 10314 | MEM 11095 | WILLIAMS' MEDIUM E 12251 |
|---|---|---|---|---|
| INORGANIC SALTS: | | | | |
| $CaCl_2$ (anhyd.) | 200.00 | 200.00 | 200.00 | 200.00 |
| $CuSO_4.5H_2O$ | — | — | — | 0.0001 |
| $Fe(NO_3)_3.9H_2O$ | 0.10 | 0.10 | — | 0.0001 |
| KCl | 400.00 | 400.00 | 400.00 | 400.00 |
| $MnCl_2.4H_2O$ | — | — | — | 0.0001 |
| $MgSO_4$ (anhyd.) | 97.67 | 97.67 | 97.67 | 97.67 |
| NaCl | 6,400.00 | 6,400.00 | 6,800.00 | 6,800.00 |
| $NaHCO_3$ | 3,700.00 | 3,700.00 | 2,200.00 | 2,200.00 |
| $NaH_2PO_4.H_2O$ | 125.00 | 125.00 | 140.00 | — |
| $NaH_2PO_4$ | — | — | — | 140.00 |
| $ZnSO_4.7H_2O$ | — | — | — | 0.0002 |
| OTHER COMPONENTS: | | | | |
| D-Glucose | — | 4,500.00 | 1,000.00 | 2,000.00 |
| Glutathione | — | — | — | 0.05 |
| Methyl Linoleate | — | — | — | 0.03 |
| Phenol red | 15.00 | 15.00 | 10.00 | 10.00 |
| Sodium Pyruvate | — | — | — | 25.00 |
| AMINO ACIDS: | | | | |
| L-Alanine | — | — | — | 90.00 |
| L-Arginine.HCl | 84.00 | 84.00 | 126.00 | — |
| L-Arginine | — | — | — | 50.00 |
| L-Asparagine.$H_2O$ | — | — | — | 20.00 |
| L-Aspartic Acid | — | — | — | 30.00 |
| L-Cysteine | — | — | — | 40.00 |
| L-Cystine | — | 48.00 | — | — |
| L-Cystine.2HCL | 63.00 | 63.00 | 31.00 | 26.10 |
| L-Glutamine | 584.00 | 584.00 | 292.00 | — |
| L-Glutamic Acid | — | — | — | 50.00 |
| Glycine | 30.00 | 30.00 | — | 50.00 |
| L-Histidine.HCl.$H_2O$ | 42.00 | 42.00 | 42.00 | — |
| L-Histidine | — | — | — | 15.00 |
| L-Isoleucine | 105.00 | 105.00 | 52.00 | 50.00 |
| L-Leucine | 105.00 | 105.00 | 52.00 | 75.00 |
| L-Lysine.HCl | 146.00 | 146.00 | 73.00 | 87.50 |
| L-Methionine | 30.00 | 30.00 | 15.00 | 15.00 |
| L-Phenylalanine | 66.00 | 66.00 | 32.00 | 25.00 |
| L-Proline | — | — | — | 30.00 |
| L-Serine | 42.00 | 42.00 | — | 10.00 |
| L-Threonine | 95.00 | 95.00 | 48.00 | 40.00 |
| L-Tryptophan | 16.00 | 16.00 | 10.00 | 10.00 |
| L-Tyrosine.2Na.$2H_2O$ | 104.00 | 104.00 | 52.00 | 50.70 |
| L-Valine | 94.00 | 94.00 | 46.00 | 50.00 |
| VITAMINS: | | | | |
| Ascorbic Acid | — | — | — | 2.00 |
| Biotin | — | — | — | 0.50 |
| D-Ca pantothenate | 4.00 | 4.00 | 1.00 | 1.00 |
| Choline chloride | 4.00 | 4.00 | 1.00 | 1.50 |
| Ergocalciferol | — | — | — | 0.10 |
| Folic acid | 4.00 | 4.00 | 1.00 | 1.00 |
| i-inositol | 7.20 | 7.20 | 2.00 | 2.00 |
| Menadione | — | — | — | 0.01 |
| Na Bisulfate | | | | |
| Niacinamide | 4.00 | 4.00 | 1.00 | 1.00 |
| Pyridoxine HCl | — | 4.00 | — | — |
| Pyridoxal HCl | 4.00 | — | 1.00 | 1.00 |
| Riboflavin | 0.40 | 0.40 | 0.10 | 0.10 |
| α-Tocopherol Phosphate Disodium | — | — | — | 0.01 |
| Thiamine.HCl | 4.00 | 4.00 | 1.00 | 1.00 |
| Vitamin A Acetate | — | — | — | 0.10 |
| Vitamine $B_{12}$ | — | — | — | 0.20 |

In accordance with the preferred embodiment of present invention, the following supplemental components in Table II are added to the stock basal media of Table I in a total volume of 1000 ml. The preferred amounts listed coincide with those described below in the Example for which the basal stock medium was constructed from 445 ml of DMEM 10314 and 555 ml 11966 to provide a D-glucose concentration of 2.0 g/L such that no additional D-glucose was added. It is to be understood that when using other basal stock media the optimal amounts of these components that are added may vary.

TABLE II

Additions to SM for HBM

| | Preferred Amount units/L | Concentration Range units/L |
|---|---|---|
| D-Galactose | 2.0 g | 0.01–5.0 g* |
| D-Glucose | 2.0 g** | 0.01–5.0 g* |
| Nicotinamide | 610.0 mg | 1–3050 mg |
| L-Proline | 30.0 mg** | 1–120 mg |
| L-Arginine | 84.0 mg** | 1–150 mg |
| L-Ornithine | 100 mg | 1–500 mg |
| human-holo-Transferrin (3% Fe saturated) | 5.0 mg | 0.1–100 mg |
| h-Insulin | 5.0 mg | greater than $10^{-11}$ M |
| Dexamethasone | $1 \times 10^{-7}$ M | $10^{-12}$–$10^{-3}$ M |
| $ZnCl_2$ | .544 mg** | 1–3000 μg |
| $MnSO_4$ | 0.025 mg** | 1–250 μg |
| $ZnSO_4.7H_2O$ | .750 mg** | 1–3000 μg |
| $CuSO_4.5H_2O$ | 0.20 mg** | 1–1000 μg |
| Selenium | 5.0 μg | 1–150 μg |
| L-Glutamine*** (additional to SBM) | 5.0 mM | 2.0–10.0 mM |
| HEPES | 20.0 mM | 5–50 mM |

*If both D-galactose and D-glucose are used, the upper limit is about 8.0 g/L or less, taking into consideration the amounts present in the particular stock basal medium used, if any. The lower limit for when both or only one of D-glucose or D-galactose is used is about 0.01 g/L or greater. For example, in the Example herein, the blended DMEM medium used contained 2.0 g/L D-glucose with no additional amount added, and 2.0 g/L D-galactose was added.
**If not already in SM stock basal medium.
***L-glutamine is a required nutrient in the present invention. Many stock basal medias are provided with L-glutamine included. However, it is well known by practitioners of the art of cell culture that L-glutamine will degrade by oxidation, such that all L-glutamine will be degraded over a period of a few weeks following manufacture. Therefore, additional L-glutamine is added to the HBM medium of the present invention as described to compensate for this.

Table III below lists substances which may be optionally added to HBM medium to optimize cell growth for specific purposes and for specific species origin of hepatocytes and specific cell lines or malignant cells. Again, these amounts will vary depending on whether a particular component is already present in the stock basal medium being used.

TABLE III

Optional Additives for HBM

| | Preferred Amount units/L | Concentration Range units/L |
|---|---|---|
| Albumin* | 2.0 g | 0–10.0 g |
| Penicillin** | 100 U | 0–2500 U |
| Streptomycin** | 100 μg | 0–2500 μg |
| Sodium Pyruvate | 0.15 g | 0–2.0 g |
| Gamma Tocopherol | 0.35 mg | 0–3.5 mg |
| Alpha Tocopherol | 0.15 mg | 0–2.5 mg |
| Vitamin $D_3$ | 0.20 mg | 0–1.8 mg |

TABLE III-continued

Optional Additives for HBM

|  | Preferred Amount units/L | Concentration Range units/L |
|---|---|---|
| Dextran* | 2.0 g | 0–5.0 g |
| Iron Gluconate*** | 25.0 µg | 0–100 µg |
| Linolenic Acid | 1.0 g | 0–5.0 g |
| Apo-transferrin*** | 5.0 mg | 0–20.0 mg |
| Retinol | 0.05 mg | 0–2.0 mg |
| Vitamin $B_{12}$ | 0.15 mg | 0–2.0 mg |
| Ascorbic acid | 3.0 mg | 0–10.0 mg |
| Choline Chloride | 1.5 mg | 0.2–12.5 mg |
| Biotin | 0.75 mg | 0.2–15.0 mg |

*Dextran can be substituted for albumin.
**Other antibiotics may be used, such as for example, gentamycin.
***Iron gluconate and apo-transferrin can be substituted for iron-saturated holo-transferrin.

In instances where accelerated growth is desired various growth factors can be added to the HBM of the present invention. While HGF/SF, EGF, and TGFα are presently preferred, it is to be understood that other growth factors may also be used. The preferred amount of such growth factors typically vary with the particular source used. The amounts listed herein are therefore necessarily limited to the particular sources used herein. In the Example below HGF/SF was preferably added to HBM at 40 ng/ml; EGF was preferably added at 20 ng/ml; and TGFα was preferably added at 20 ng/ml.

The following examples are included for illustrative purposes only and are not intended to limit the scope of the invention.

EXAMPLE

Materials and Methods

Materials

Male Fischer 344 rats from Charles River, (Pennsylvania) were used for all the experiments involving rat hepatocyte isolation. EGF and Matrigel (a mixture of matrix components derived from EHS mouse tumor) were obtained from Collaborative Research (Waltham, Mass.). [$^3$H]Thymidine was obtained from ICN Radiochemicals (Irvine, Calif.). Collagenase for hepatocyte isolation was obtained from Boehringer Mannheim (Indianapolis, Ind.). Vitrogen (Celtrix Labs, Palo Alto, Calif.) was used for the construction of the collagen gels. General reagents were obtained from Sigma Chemical Co. (St. Louis, Mo.). HGF/SF used for these studies was the AS variant. ECL matrix was purchased from Upstate Biotechnology (Lake Placid, N.Y.).

Isolation and Culture of Hepatocytes

Rat hepatocytes were isolated by an adaptation of the calcium two step collagenase perfusion technique as taught by Kost, D. P., et al, *J. Cell. Physiol.* 147:274 (1991), the disclosure of which is incorporated herein by reference. All such preparations were designed to obtain a population of pure hepatocytes. Unlike many other hepatocyte culture systems, the present invention does not require or use a feeder cell co-culture or feeder-cell conditioned media. After isolation of hepatocytes, the cells were suspended in a media used for cell attachment to the culture plates. This media was MEM (GIBCO 12570) with NEAA (GIBCO 11140), insulin 5 mg/L, and gentamycin 5 µg/ml. Hepatocytes were plated on a single layer of collagen coating as described below and left to attach for 2 hours. Six-well cluster plates (9.8 square centimeters per plate) from Corning were used. For experiments where hepatocytes were not going to be induced to proliferate, or where assessments of differentiated function were performed, the cells were plated at a density of 80,000 hepatocytes per square centimeter of surface area. For experiments intended to induce proliferation or genetic transduction with foreign DNA, cells were plated at an initial density of 1,000 or 10,000 hepatocytes per square centimeter of surface area. The plating medium was replaced with the invention HBM medium at 2 hours after the cells were plated and every 48 hours thereafter. Thymidine, growth factors, and other ingredients, were added at the time of medium change as required.

Human hepatocytes were isolated by an adaptation of the collagenase perfusion technique as described by Strom, S. C., et al., *Journal of National Cancer Institute* 65(5):771–8 (1982), the disclosure of which is incorporated herein by reference. Cells were cultured as described above for the rat hepatocytes.

Collagen gels were prepared as described by Michalopoulos, G. K., et al., *Exp. Cell. Res.* 94:70 (1975), the disclosure of which is incorporated herein by reference. Dry coating of plates with collagen and Matrigel was also performed as specified by the manufacturer. Matrigel gels were made by adding 50 µl of Matrigel solution into 0.5 ml of medium directly on the top of attached cells.

DNA synthesis was measured by the uptake of tritiated thymidine into trichloroacetic acid (TCA) precipitable material as described by Kost, D. P., et al. (1991), cited above. Collagen gels, where necessary, were digested with 2 mg of collagenase per ml of MEM medium used. Incubation was then carried out for 30 minutes at 37° C. The digested gels were treated with NaOH followed by TCA to precipitate DNA, RNA, and proteins as described by Kost, D. P., et al. (1991), cited above.

Composition of the HBM Medium

DMEM, HEPES, L-glutamine, and antibiotics were purchased from GIBCO/BRL (Gaithersburg, Md.). ITS mixture (Insulin, Transferrin, Selenium) was purchased from Boehringer Mannheim. All other additives were cell culture grade (Sigma). Unless otherwise indicated for specific experiments, the stock basal medium consisted of DMEM 11966 and DMEM 10314 blended to achieve a final D-glucose concentration of 2.0 g/L. In this case, 445 ml of DMEM 10314 was blended with 555 ml of DMEM 11966 to achieve this concentration. The formulas for these stock basal media are set forth in Table I above. The resulting blended medium was then supplemented with: purified bovine albumin 2.0 g/L, D-galactose 2.0 g/L, L-ornithine 0.1 g/L, L-proline 0.030 g/L, nicotinamide 0.610 g/L, $ZnCl_2$ 0.544 mg/L, $ZnSO_4.0.7H_2O$ 0.750 mg/L, $CuSO_4.5H_2O$ 0.20 mg/L, $MnSO_4$ 0.025 mg/L, glutamine 5.0 mM, ITS (rh-insulin 5.0 mg/L, human transferrin 5.0 mg/L [30% diferric iron saturated], selenium 5.0 µg/L), dexamethasone $10^{-7}$M, and HEPES buffer 20.0 mM. Penicillin and streptomycin were added at 100 U/L and 100 µg/L, respectively. The mixed basal HBM was sterilized by filtration through a 0.22-µm low protein-binding filter system (Corning), stored at 4° C., and used within 4 weeks. The growth factors, as required, were added to HBM fresh at the specified concentrations every time the medium was changed.

Retroviral Transfection and Assessment of Clonal Expansion

Hepatocytes were initially plated at $10^4/cm^2$ and grown in HBM supplemented with HGF/SF (40 ng/ml) and EGF (20 ng/ml). After 68 hours the media was replaced with supernatant from CRψP-packaged, replication-deficient, amphotropic retrovirus (MFG~5×10$^5$ units per ml) containing the E. coli β-galactosidase gene under an LTR promoter as described by Zitvogel, L. H., et al., *Hum. Gene. Ther.* 5:1493 (1994), the disclosure of which is incorporated herein by reference. Polybrene was added at 2 μg/ml. The supernatant was replaced after 18 hours with HBM that was supplemented with EGF at 20 ng/ml and HGF/SF at 40 ng/ml. The brief exposure with the virus-containing supernatant did not have an adverse effect on hepatocyte survival or proliferation. At indicated times, cells were fixed with 0.5% glutaraldehyde in PBS for 10 min and developed with X-Gal substrate at 37° C. for 16 hours. Transduced cells expressing the E. coli gene stained positive as shown in FIGS. 4G and 4F. Appropriate controls for each component were negative for X-Gal staining.

Transmission Electron Microscopy

Samples for transmission electron microscopy (TEM) were fixed on the culture plates for 1–1.5 hours in 0.1M sodium cacodylate buffer (pH 7.4) that contained 2.5% glutaraldehyde and 2% formuldehyde. The plates were then rinsed 2 times with 0.1M sodium cacodylate buffer (pH 7.4) and 2 times with 0.1M sodium cacodylate buffer containing 5% sucrose (pH 7.4). They were held in the sucrose buffer for 1–7 days, rinsed 2 times with 0.1M sodium cacodylate buffer (pH 7.4), and then postfixed for 1 hour in 1% $OsO_4$ in 0.1M sodium cacodylate buffer. The plates were then rinsed again in buffer, and the fixed and processed collagen gels were then cut in strips with a razor blade. The strips were then transferred to glass specimen vials, dehydrated through a graded series of ethanol (25–100%) and two propylene oxide changes, and infiltrated with Epon-Araldite resin (BioTec, Tex.). Several changes of resin were made over 2 days, as the collagen gels tended to hold the propylene oxide. The collagen strips were flat-embedded and cured overnight at 60° C.

Analysis of Gene Expression by Northern Blots

Extraction of Total RNA and mRNA from Cultures. Total RNA was extracted from unwashed cell cultures using 2.0 ml of RNAzol B (BioTec) per well and purified per the manufacturer's guidelines. RNA concentration and purity were determined by routine spectrophotometry. Size separation of 20 μg RNA per lane was completed on denaturing 1% agarose gels and transferred to nylon membranes (Amersham, Arlington Heights, Ill.) by the capillary method. After cross-linking under UV light, the membranes were hybridized overnight with specific cDNAs (as indicated in the figures) that had been labeled with [α-$^{32}$P]dCTP using an Amersham random primer kit.

Membranes were subsequently washed under high stringency conditions and exposed to XAR film (Eastman Kodak, Rochester, N.Y.) for 1–3 days. Quantification of the RNA hybridization bands were performed by laser densitometry.

Sources of cDNA Probes cDNA probes used to study gene expression were obtained as gifts, and are available upon request from the following sources: Cytokeratin 8 from Dr. Norman Marceau (Laval University); Cytokeratin 14 from Dr. Dennis Roop (Baylor College of Medicine); Cytokeratin 18 from Dr. Robert Oshima (LaJolla Cancer Research Foundation); Cytokeratin 19 from Dr. Andre Royal (University of Montreal); TGFα (rat) originated from Dr. David Lee (University of North Carolina at Chapel Hill); EGF-R (rat) originated from Dr. Sheldon Earp (University of North Carolina at Chapel Hill); aFGF from American Type Culture Collection (ATCC) (catalog No. 78222); aFGF-R from ATCC (catalog No. 65796); uPA originated from Dr. Jay Degen (University of Cincinnati); cytochrome IIB1 from Dr. Steve Strom (University of Pittsburgh); cDNAs for albumin, a fetoprotein, and transcription factor analysis were generated by Dr. Joe Locker (University of Pittsburgh).

RESULTS OBTAINED

Role of Media Components and Matrix Substrates on Cell Proliferation

The full description of the HBM medium is given above. To evaluate the relative importance of different media components several experiments were performed whose results are shown in Table IV (A, B, and C) below. The components D-glucose, albumin, dexamethasone, transferrin and selenium, nicotinamide, and trace elements were individually subtracted from the full HBM medium composition as shown in Table IV A. The total DNA per culture after 14 days of growth is shown therein. As can be readily seen, removal of dexamethasone had the most dramatic effect, followed by removal of nicotinamide. In Table VI B, growth of cells achieved by day 14 is compared between HBM medium containing diferric transferrin (iron saturated) versus iron unsaturated transferrin. Addition of iron containing diferric transferrin (30% saturation) was found to be much more effective in promoting growth. The addition of elemental iron ($FeSO_4$, 0.1 μM) to the unsaturated transferrin failed to overcome the difference. Table VI C provides information on the relative effects of D-glucose, D-galactose, and L-ornithine in HBM medium. All three of these components are potential sources of energy to the cells. Complete cessation of growth was noticed when all three components were removed. Addition of D-glucose alone restored most of the response whereas the addition of D-galactose alone was less effective. Ornithine alone had minimal effect. Concentrations of 2 g per liter each of albumin and D-glucose were found to be optimal though the effects were not statistically different than 1 or 3 g per liter in each case. The effect of complete removal of these components is shown in Table IV A.

TABLE IV

| | μg/well |
|---|---|
| A. Effect of Removal of Specific HBM Components on Hepatocyte Growth | |
| Zero time DNA | 13.90 ± 3.60 |
| DNA at day 14 in HBM (with HGF/SF and EGF) supplemented with: | |
| + All components | 84.90 ± 0.50 |
| − Glucose | 69.80 ± 2.90 |
| − Albumin | 68.70 ± 0.50 |
| − Dexamethasone | 13.70 ± 0.20 |
| − (Transferrin and selenium) | 63.10 ± 2.00 |
| − Nicotinamide | 35.20 ± 1.70 |
| − Trace elements | 65.00 ± 2.40 |
| − All components | 20.20 ± 4.30 |
| B. Effects of Iron and Transferrin on Hepatocyte Growth | |
| Zero time DNA | 9.21 ± 1.01 |
| Diferric transferrin (iron saturated) | 70.15 ± 1.21 |
| Diferric transferrin plus added iron (5 μM) | 1.83 ± 0.41 |
| Iron poor transferrin | 24.84 ± 4.30 |
| Iron poor transferrin with added iron | 1.10 ± 0.90 |
| C. Effect of Removal of Glucose, Ornithine, or Galactose | |
| Zero time | 11.0 ± 0.4 |
| Control (Gluc.+,Orn.+,Gal+) | 59.0 ± 2.5 |

TABLE IV-continued

| | μg/well |
|---|---|
| Gluc.−,Orn.−,Gal.− | 10.6 ± 0.8 |
| Gluc.−,Orn.+,Gal.− | 14.4 ± 0.9 |
| Gluc.−,Orn.−,Gal.+ | 44.2 ± 6.0 |
| Gluc.+,Orn.−,Gal.− | 59.0 ± 4.0 |
| Gluc.+,Orn.+,Gal.− | 62.7 ± 1.4 |
| Gluc.+,Orn.−,Gal.+ | 63.6 ± 0.3 |

The indicated HBM components were removed and hepatocyte were grown in the modified media for 14 days. The total DNA per culture in micrograms was measured at day 14 to evaluate growth cell growth. Time zero was the sample of hepatocyte suspension that was inoculated into the plate immediately after cell isolation. The data are expressed as mean ± standard error of three separate plates.

Hepatocytes Enter Diffusely into Proliferation under the Influence of HGF/SF, EGF, and TGFα

Figure 1B:
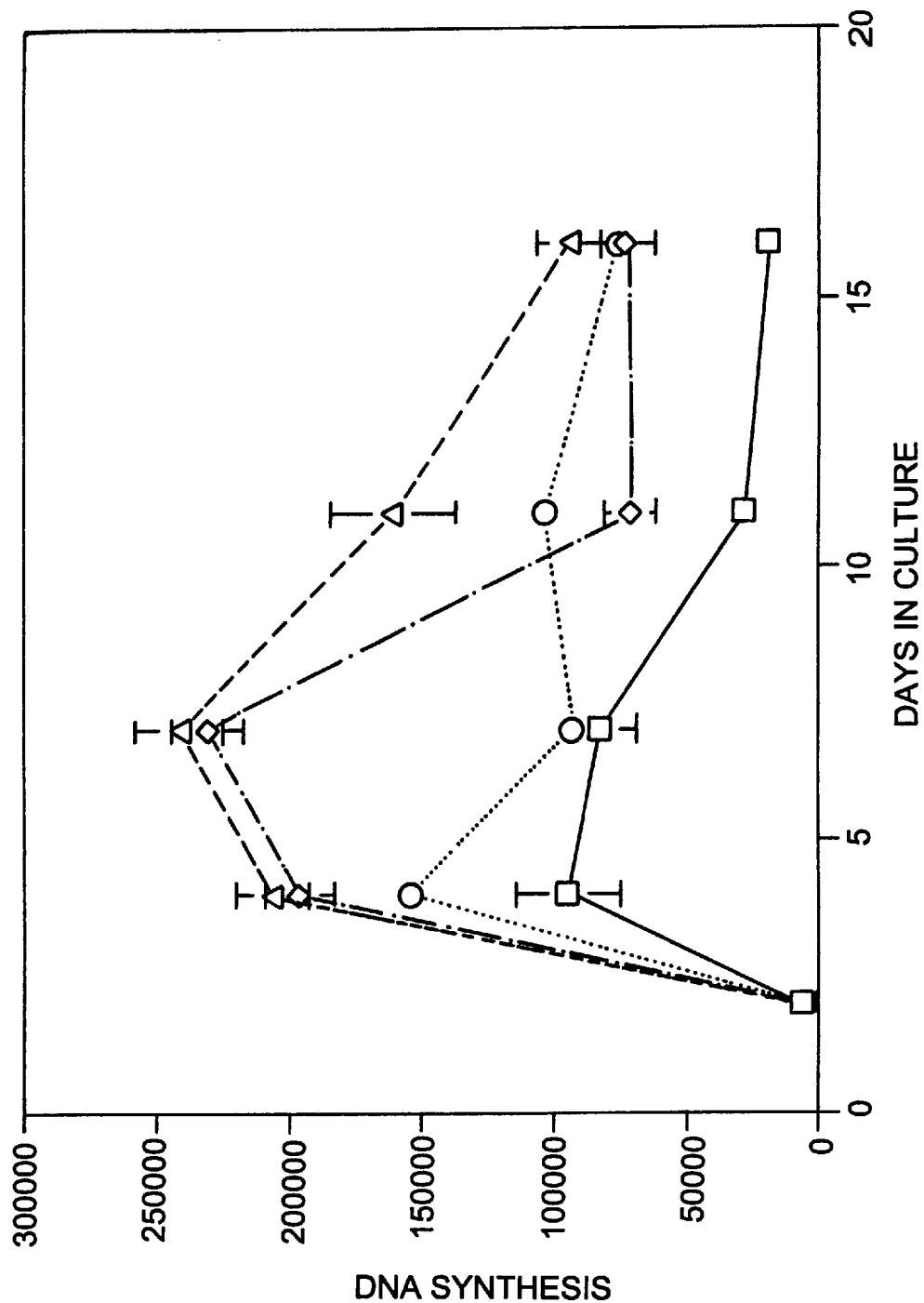

FIGS. 1A and 1B show the uptake of thymidine per μg DNA, as well as the BRdU nuclear labeling index at different days in culture in cells growing in the presence of HGF/SF and EGF (40, 20 ng/ml respectively) as described above. As can be seen, most of the proliferation occurs at days 5–12. By day 15 the cultures were confluent and DNA synthesis slowed down. The high nuclear labeling index during the times of sustained proliferation indicates that the proliferating cells derive directly from the mature hepatocytes.

Figure 1C:
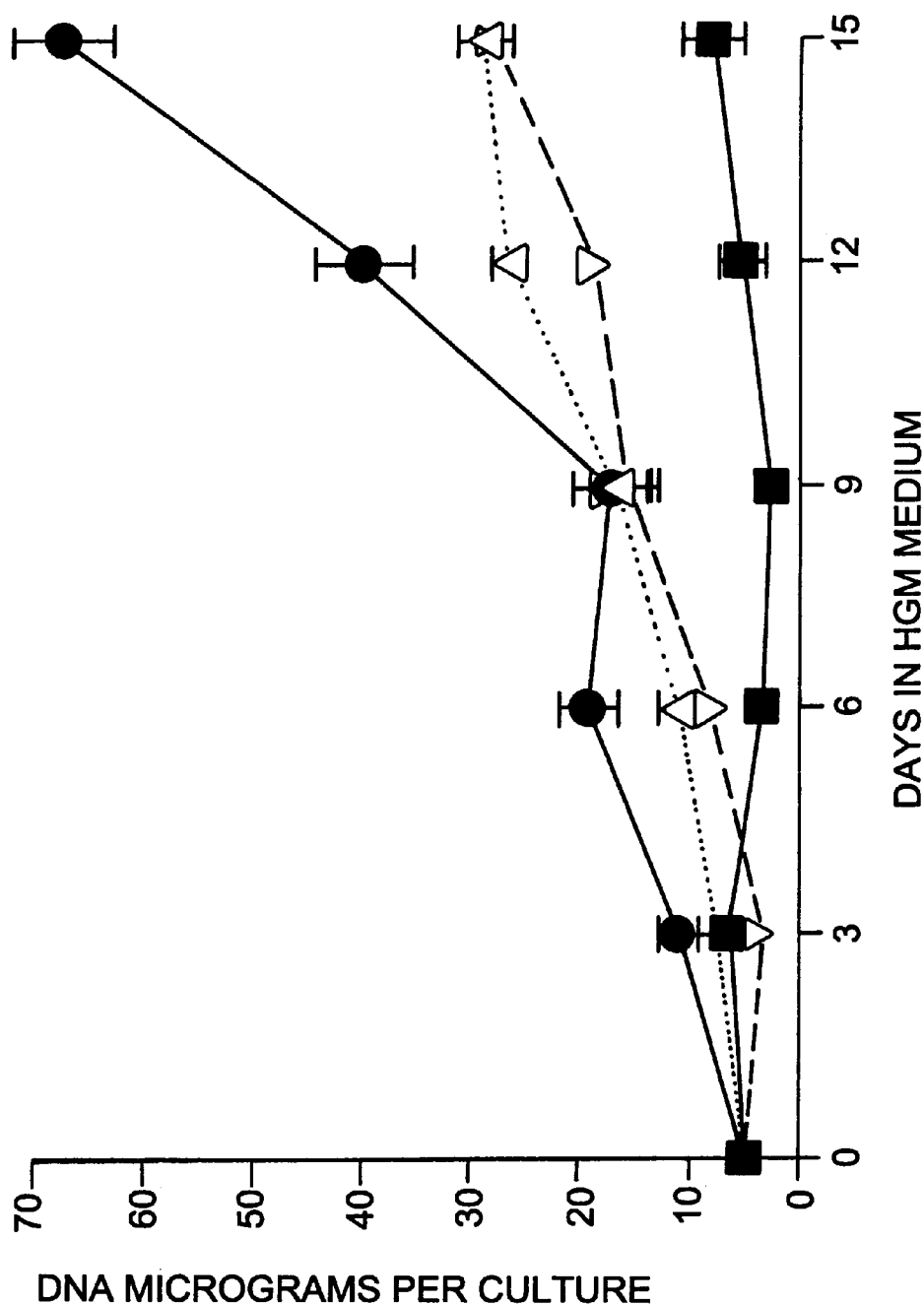
Figure 2:
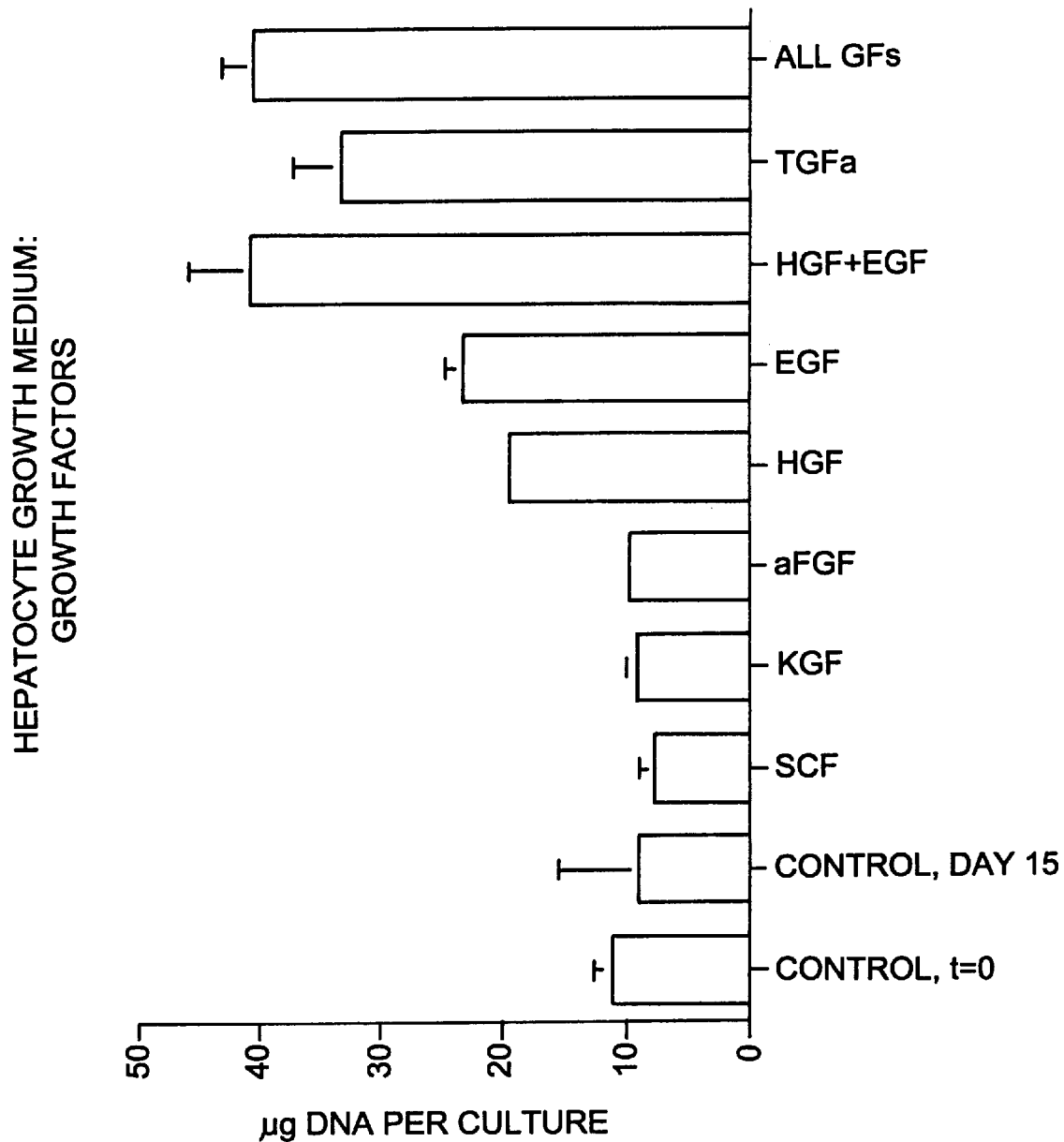
FIG. 2 is a graph showing the day 15 DNA per plate of rat hepatocytes grown in HBM with the indicated growth factors. Cells represented by control (day t=0) and day 15 were grown in HBM without any growth factors.

The growth factors HGF/SF, EGF, TGFα, KGF (keratinocyte growth factor), SCF (stem cell factor), and aFGF (acidic fibroblast growth factor) were added individually to HBM medium. Of the growth factors added, HGF/SF, EGF, and TGFα (shown in FIG. 2 as "TGFa") caused significant cell proliferation, as shown by the total amount of DNA per culture at day 15. KGF, aFGF, and SCF when added alone or in combination had no proliferative effect as shown in FIG. 2. TGFα had a stronger proliferative effect than any of the other mitogens when added alone to HBM medium. HGF/SF and EGF together had the strongest proliferative effect for a given time interval of 15 days together than did any other single mitogens or combinations. Addition of all the growth factors together had no more effect than the combined HGF/SF and EGF as seen in FIG. 2. The detailed cell kinetics induced by HGF/SF and EGF alone or in combination are shown in FIG. 1C. The total DNA per culture is shown as a function of the time in culture. The largest amount of accumulated DNA at day 15 was seen with the combination of HGF/SF and EGF. The DNA per culture at day 15 was 12 times that at time 0, reflecting the increase in cell number. HGF/SF and EGF were about equally potent.

TGFα alone was more mitogenic than either HGF/SF or EGF alone.

Effect of Matrix Substrates

Figure 3:
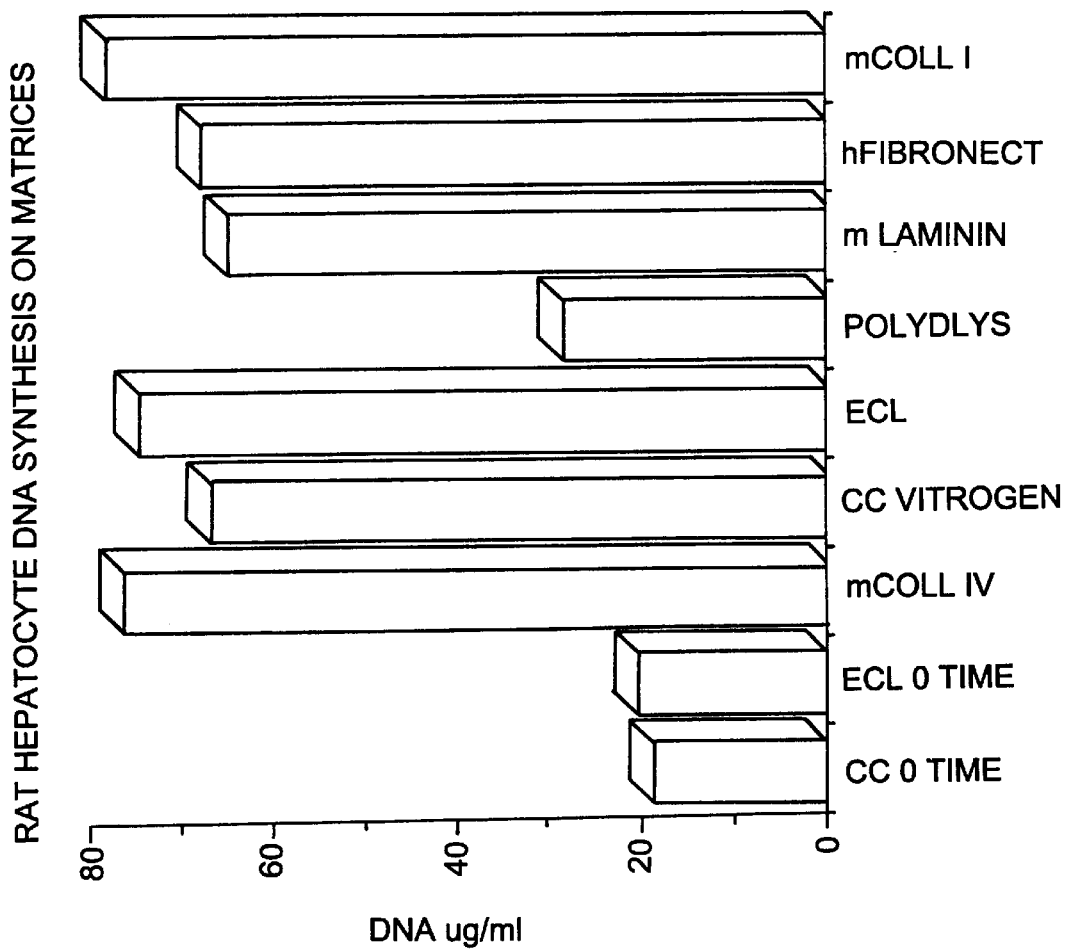
FIG. 3 is a graph showing the amount of DNA synthesis per plate (μg/culture) of rat hepatocytes at day 15 in HBM supplemented with HGF/SF and EGF grown on different matrices. "CC" means collagen coated; "ECL" is a commercial matrix; "m COLL IV" means mouse collagen IV; "CC VITROGEN" means bovine skin collagen type I; "POLY D LYS" means poly D-Lysine; "m LAMININ" means mouse laminin; "h FIBRONECT" means human fibronectin; and "m COL I" means mouse collagen I.

Several matrix substrates promoted cell growth in this system. Rat hepatocytes were cultured for 15 days in HBM supplemented with HGF/SF (40 ng/ml) and EGF (20 ng/ml) grown on various matrices as seen in FIG. 3. The cells were cultured as described above. Dry coating with collagens type IV (mouse), type I (bovine), fibronectin, and laminin were equally effective in promoting cell growth as assayed by measurement of total DNA per culture at day 15. Dry coating with ECL (a commercial derivative of EHS gel, UBI) had superior effects. Coating with type I collagen (Vitrogen commercial preparation) was the standard method used for the experiments unless otherwise specified. The effect of matrix gels in promoting specific phenotypic conversions in these cultures is further discussed below.

Phenotypic Changes of Hepatocytes During Proliferation

The morphology of the proliferating cells (cultured in HBM as described above supplemented with 40 ng/ml HGF/SF and 20 ng/ml EGF) varied at different times after the stimulation of cell proliferation. From a normal hepatocyte morphology as seen in FIG. 4A, the proliferating cells in the first 4 days acquired long projections assuming the phenotype typically described as due to the "scattering" effect of HGF/SF on hepatocytes as seen in FIG. 4B as described by Michalopoulos, G. K., et al, *J. Cell. Physiol.* 156:443 (1993), the disclosure of which is incorporated herein by reference. Between days 6 and 8, the proliferating cells lost most of their cytoplasmic granules, the nuclei became less prominent, the projections diminished and the cells began to grow as monolayer patches. Eventually these patches merged as the cells continued to grow to form a continuous monolayer as seen in FIG. 4C. Examination by electron microscopy seen in FIGS. 4D and 4E showed that most of the features typical of mature hepatocytes were missing. By day 15 there were no lamallae of endoplasmic reticulum wrapping around mitochondria and there are no glycogen rosettes or peroxisomes. Bile canaliculi were absent. There was a prominent increase in bundles of keratin intermediate filaments. The nuclei were angular with very prominent nucleoli. After confluency the morphology gradually revert back to mature differentiated hepatocytes with endoplasmic reticulum lamallae, mitochondria, glycogen, peroxisomes, bile canaliculi, etc., similar to that in FIGS. 6B and 6C.

Clonal growth of the proliferating rat hepatocytes is demonstrated in FIGS. 4F and 4G. Hepatocytes were transfected at day three in culture with a replication-deficient retrovirus containing the lac-Z gene under the influence of a viral LTR and were stained for expression of β-galactosidase. Mostly single cells were stained positive at day four in culture (1 day after transfection) as seen in FIG. 4F. On the other hand, staining at day 10 and continuing through day 28 showed patches of positive-stained, hepatocytes, consistent with clonal growth of the original transfected hepatocytes as seen in FIG. 4G. The percentage of lac-Z-positive cells (~20%) did not appear to change during culture.

Proliferating Hepatocytes Express Altered Levels of Various Genes

Figure 5A:
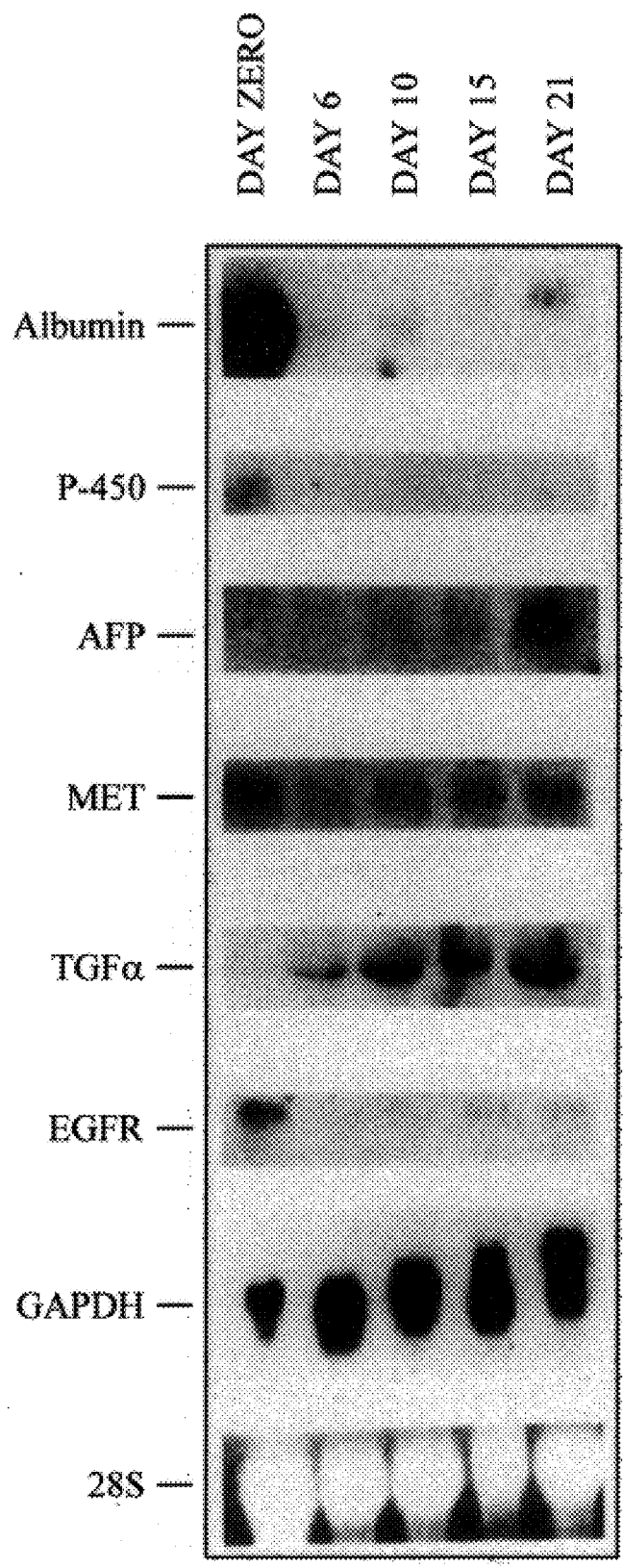
FIGS. 5A and 5B are photographs of Northern blots showing expression of specific genes at different days in rat hepatocyte cultures maintained in HBM in the presence of HGF/SF and EGF as described herein. GAPDH expression and the intensity of the 28S RNA after ethidium bromide staining were used as internal controls.

The expression of several specific genes was assayed in proliferating hepatocytes. These included mRNA genes associated with hepatocyte differentiation (albumin, ctyochrome IIB1 (labeled as P450 in FIG. 5A)), genes encoding cytokeratin markers (cytokeratins 14, 18, and 19) or related to hepatocyte growth (urokinase (uPA), HGF/SF and its receptor c-met (labeled as MET in FIG. 5A), EGF (labeled as EGFR) and TGFα and their receptor, acidic FGF and its receptor, and TGFβ1). These genes were studied by Northern blot analysis of RNA from cultures grown in the presence of either combined HGF/SF (40 ng/ml)and EGF (20 ng/ml) (FIGS. 5A and 5B) or with TGFα alone (20 ng/ml) (data not shown). Total RNA was isolated from cultures at days 0, 6, 10, 15, and 21. No expression of HGF/SF or TGFβ1 mRNA was seen at any of the time points examined.

As can be seen, albumin and cytochrome IIB1 mRNA were present at time zero and subsequently decreased. Albumin mRNA increased by day 21 at which time mRNA for α feto protein (AFP) was also detected. mRNA for cytokeratins, 14, 18, and 19 increased through culture. There was a steady increase in mRNA for aFGF and TGFα. The mRNA of receptors for HGF/SF (MET, FIG. 5A) and aFGF (FIG. 5B aFGFR) remained present throughout the culture time. The EGF receptor (EGFR) mRNA declined from day zero but remained expressed. CAPDH mRNA expression was used as a reference "housekeeping" gene. Dramatic increases were noted in expression of urokinase as well as cytokeratins 14 and 19. Some differences from the above pattern were seen in the cultures that, instead of HGF/SF and EGF, were maintained in the presence of TGFα (20.0 ng/ml). In these cultures albumin expression and expression of the HGF/SF receptor were better preserved during proliferation whereas AFP appeared earlier. (Data not shown.) Despite the observed differences in gene expression patterns no morphologic differences were seen between cells growing in the presence of TGFα or HGF/SF plus EGF, once confluency was achieved.

Figure 5B:
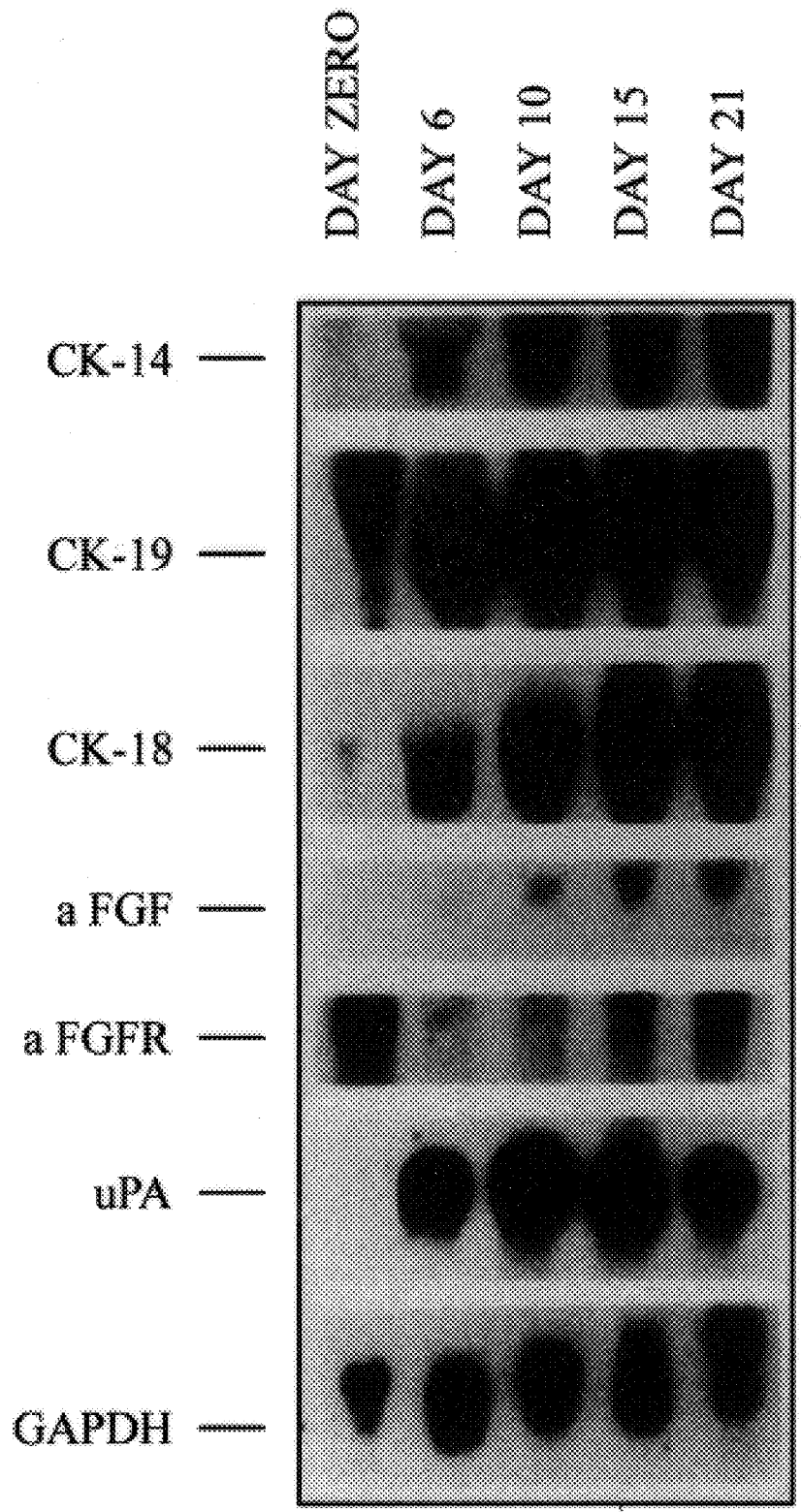
Figure 6A:
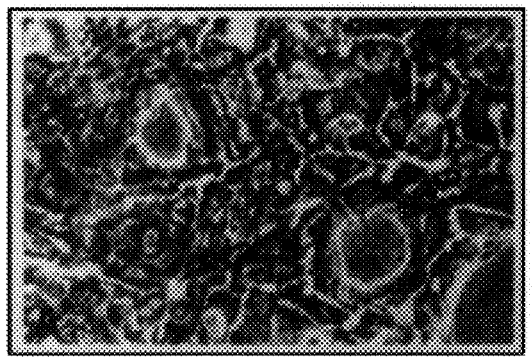
FIGS. 6A–6F are photographs of proliferating rat hepatocytes cultured in HBM medium in the presence of HGF/SF and EGF as described herein and Northern blots thereof.
Figure 6B:
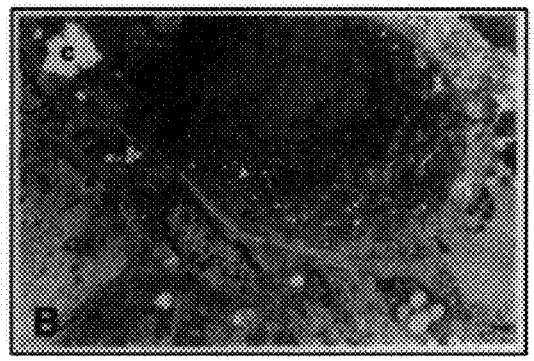
Figure 6C:
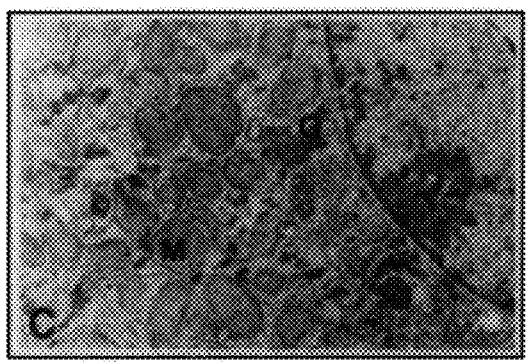
Figure 6D:
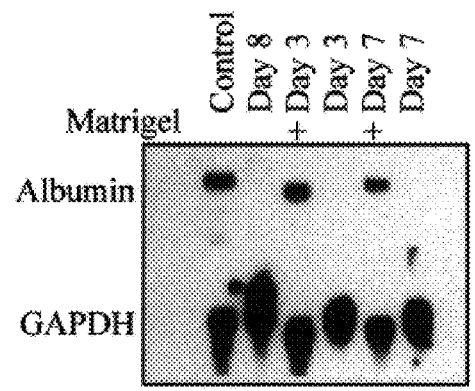
Figure 6E:
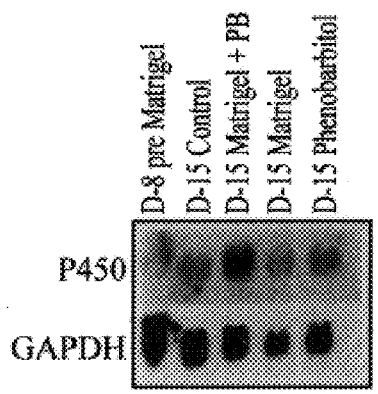
Figure 6F:
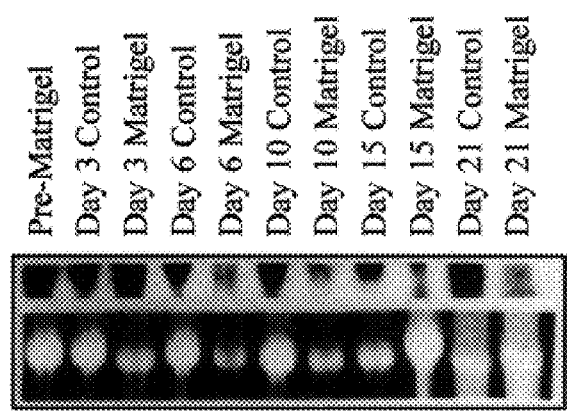

Proliferating Hepatocytes Revert to Mature Hepatocytes under the Influence of Matrigel or in the Presence Nonparenchymal Cells or With Time in Culture When Matrigel was overlaid on cultures at day 8, there was a rapid (within 2 days) appearance of bile canaliculi and organization of the cells into cord-like structures. The features of these cells are shown in FIG. 6A. As shown by electron microscopy in FIGS. 6B and 6C, these cells had typical markers of mature hepatocytes, including wrapping of the endoplasmic reticulum around mitochondria, bile canaliculi, and the presence of glycogen. Preparations of mRNA were made from cultures exposed to Matrigel for 10 days (days 8–18 in culture). The expression of albumin was compared between day zero in culture (immediately after collagenase perfusion), at day 8 in culture (before the overlay by Matrigel), and cultures at day 3 and 7 after Matrigel overlay as shown in FIG. 6D. Addition of Matrigel caused dramatic increases in expression of albumin mRNA, compared to control proliferating cultures in which it was minimally detectable. The effect of Phenobarbitol (PB) on the levels of cytochrome P450 IIB1 mRNA in the Matrigel-treated cultures was also measured as shown in FIG. 6E. Matrigel was added to the cultures at day 8. PB was added 2 days later (day 10 of culture). The cells were harvested 5 days after addition of PB (day 15 in culture). Addition of PB induced cytochrome IIB1 mRNA only in the Matrigel-treated cultures. Induction of this mRNA by phenobarbitol is typical of hepatocytes and does not occur in any other cell as reported by Michalopoulos, G., et al., Science (Wash, D.C.) 193:907 (1976), the disclosure of which is incorporated herein by reference. Typically, hepatocyte cultures rapidly lose the capacity to respond to PB. This finding is supporting evidence that addition of Matrigel to the cultures of proliferating hepatocytes induces a mature hepatocyte phenotype, as attested to by the electron microscopic structure shown in FIGS. 6B and 6C. The expression of cytokeratin 19 (CK19) (FIG. 6F), a bile duct marker expressed by the proliferating hepatocytes before introducing differentiating conditions, also ceased expression after addition of Matrigel as seen in FIG. 5B.

DNA synthesis was measured in the cultures exposed to Matrigel and there was a substantial decrease. To assess whether differentiation to mature hepatocyte morphology required DNA synthesis, 20 mM hydroxurea was added to the HBM media. This has been shown (Michalopoulos, G. K., et al., Cancer Res. 38:1866 (1978), the disclosure of which is incorporated herein by reference) to abolish scheduled semiconservative DNA synthesis in hepatocytes by inhibiting ribonucleotide reductase. Hydroxyurea was added to cultures before the Madrigel overlay and maintained throughout the next 5-day period. DNA synthesis decreased down to 3.93% of the control (without hydroxyurea) in the proliferating cultures maintained in the absence of Matrigel and down to 6.27% of control (without hydroxyurea) in the cultures maintained in the presence of Matrigel. Though DNA synthesis was decreased down to 6.27% of control (+Matrigel, no hydroxyurea) levels, the conversion of the proliferating hepatocytes to mature hepatocyte morphology was entirely unaffected and involved the entire population.

Figure 7A:
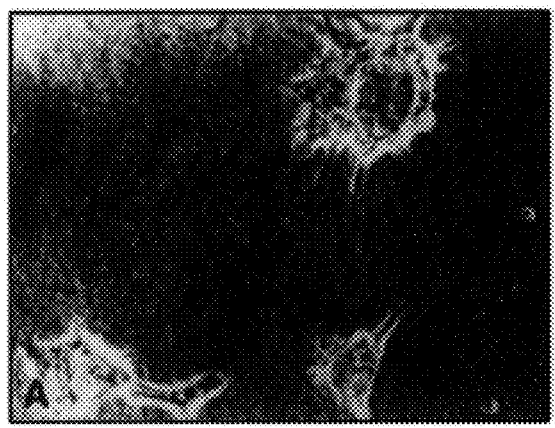
FIGS. 7A–7E show the results of studies showing formation of ductular/acinar structures in cultures of rat hepatocytes kept from the beginning of culture between two type I collagen gel layers in HBM in the presence of HGF/SF. The FIGS. 7A–7D photographs are of 15 day cultures.
Figure 7B:
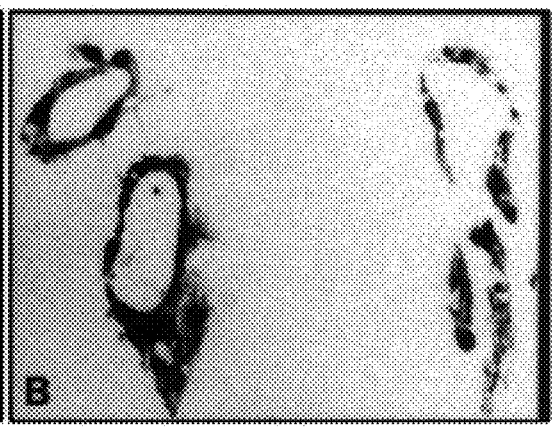
Figure 7C:
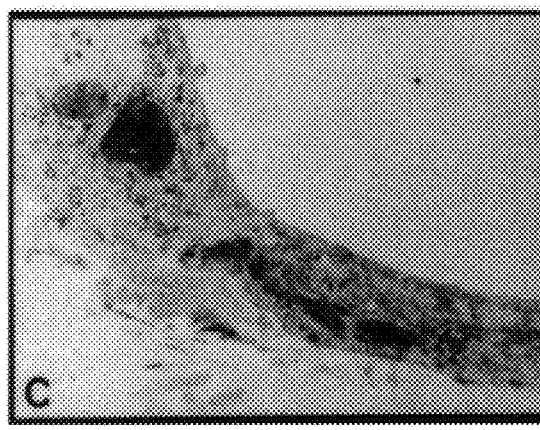
Figure 7D:
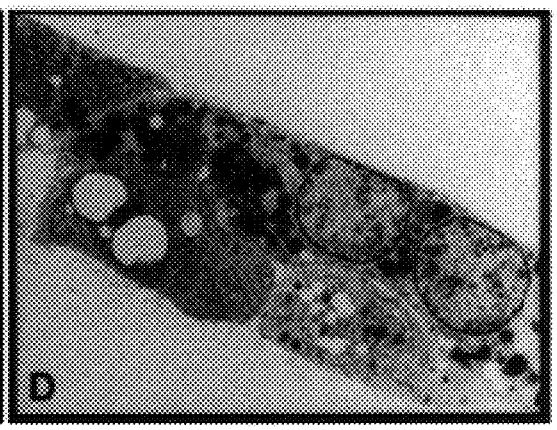
Figure 7E:
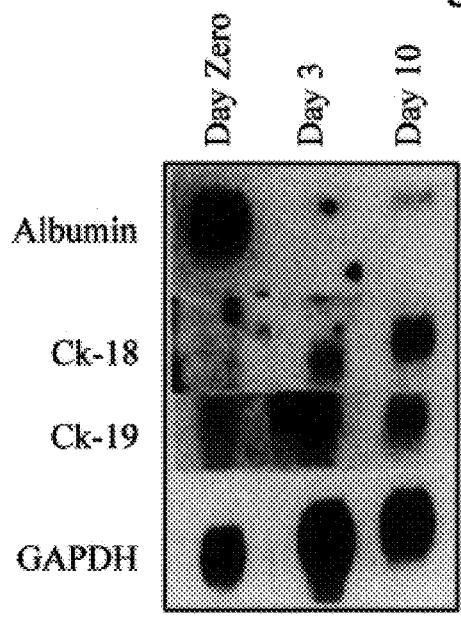

HGF/SF (but Not TGFα or EGF) Induces Proliferating Hepatocytes to Differentiate into Ductular/Acinar Structures in Type I Collagen Gels Hepatocytes maintained between two collagen gel layers retain their morphology and differentiation for prolonged time periods as described by Michalopoulos, G. K., et al., J. Cell. Physiol. 156:443 (1993), the disclosure of which is incorporated herein by reference. Hepatocytes maintained in collagen gel sandwiches in cultures with convential media containing HGF/SF undergo intense proliferation, form prominent projections, and eventually become organized in structures reminiscent of the hepatic plates. The behavior of hepatocytes maintained between two layers of collagen gel as previously described was examined, but in the presence of HBM supplemented with either HGF/SF or EGF as described above. It was noted that in the EGF supplemented media hepatocytes underwent the typical phenotypic transitions as described above. On the other hand, in hepatocytes in HBM supplemented with HGF/SF alone, following expansion of cells identical in appearance to the proliferating hepatocytes described above, there appeared multiple duct-shaped structures between days 10 and 15. These became prominent and encompassed most of the cells present in the cultures. Starting from approximately day 10 and by day 15 most of the cells in the culture were arranged in such ductular structures. The appearance of these structures is shown in FIG. 7A. Histologic sections are shown in FIG. 7B (light microscopy) and FIGS. 7C and 7D (electron microscopy). The structures had a ductular or acinar configuration. Some of the cells surrounding these structures were very attenuated and had light and electron microscopic appearance identical to bile duct epithelium. Others however are larger and resemble more closely the ductular hepatocytes described in previous studies of in vivo models. The proliferation of cells (data not shown) under either EGF or HGF/SF in the collagen gel sandwiches was much less (<25% at the highest peak) than that seen in the cultures on plastic coated with dry collagen. Most proliferation ceased by day 10 and the duct-like structures appeared after cell proliferation had ceased (days 10–15). Ductular acinar structures were also noted in these cultures when HGF/SF and EGF were combined but were fewer than with HGF/SF alone. As with the Matrigel overlay, additional of hydroxyurea to inhibit DNA synthesis (inhibition down to 5.1% of control) did not affect the formation of the ductular structures (data not shown). FIG. 7E shows that these cells express cytokeratin 19 which is characteristic of duct cells. (See, Sirica, A. E., Prog. Liver Dis. 10:63 (1992) and Sirica, A. E., Histol. Histopathol. 10:433 (1995), the disclosures of which are incorporated herein by reference.) A small amount of albumin expression was also retained, consistent with the presence of hepatocyte-like cells within the ductular structures as seen in FIG. 7D. It was noted that the ductular cells maintain CK19 expression in the nonproliferating state (FIG. 7F) in contrast to the cells differentiating toward the mature hepatocyte lineage which cease expressing this bile duct marker.

Figure 8:
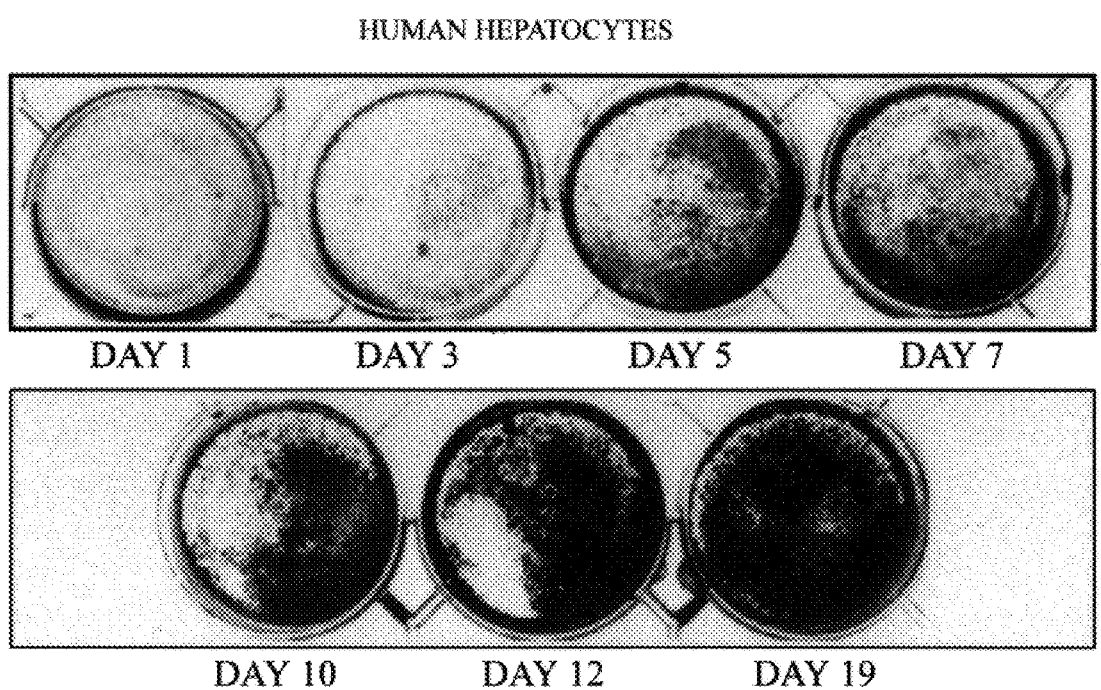
FIG. 8 shows photographs of stained human hepatocyte cultures grown in HBM supplemented with HGF/SF and EGF as described herein taken at day 1, 3, 5, 7, 10, 12, and 19

Sustained Growth and Population Expansion of Human Hepatocytes in HGM, in the Presence of HGF/SF and EGF Though human hepatocytes cultures have not been characterized as extensively as those of the rat, the literature available has shown that these cells also undergo a limited round of DNA synthesis after stimulation by growth factors and rapidly degenerate in culture. See, Ismail, T., et al., *Hepatology* 14:1076 (1991), the disclosure of which is incorporated herein by reference. The response of human hepatocytes to HGF/SF (40 ng/ml) and EGF (20 ng/ml) in HBM medium was studied. Results similar to those described for rat hepatocytes were found in primary cultures of human hepatocytes, as seen in FIG. 8. The human cells begin to rapidly proliferate at day 3–4 in culture and reach confluency by day 19.

As stated above, there is a present need for a media that allows hepatocytes that are cultured in vitro to expand as a cell population. The HBM of the present invention allows such expansion and therefore enables much needed research of proliferating hepatocytes. The present invention also will be useful in numerous other applications outlined below.

For example, all current methods in liver-targeted gene therapy that achieve stable, long-term expression of transferred genes require actively dividing cells during the initial transfection. Normal liver has only 1 in 20,000 hepatocytes in S phase growth on any particular day. In order to increase cell proliferation, a large portion (⅔) of the patient's liver must be removed. Subsequently the liver-targeted gene carrier source is intravascularly injected. The alternative to this drastic measure is to remove a small piece of liver (10%), culture the hepatocytes, transfect them in culture, and then reinfuse the cells back into the liver. This latter method, while safer, less expensive and better controlled than the former, is currently hampered by the lack of culture media such as HBM which allows prolonged proliferation, clonal expansion of essentially all cells cultured, and long term viability of the cells.

The design of current extracorporeal liver devices based on bioartificial liver tissue which include cellular elements rely on transformed (tumor) hepatocytes or animal hepatocytes. The animal cells do not survive for more than few days in the bioreactors that are used and do not proliferate, making it necessary to generate bioreactors more frequently and in close proximity and to maintain all necessary facilities, materials and animal donors in anticipation of need. Additionally, animal cells may have several undesirable aspects which makes them clinically difficult or dangerous to use. Also, tumor cells used in these devices carry the risk of leakage of cells into the patient and therefore potentially could give rise to tumors in the patient. The HBM media of the present invention will permit production of bioreactors containing animal and/or human hepatocytes and/or other cells and provide the unique features of increasing cell numbers while maintaining long term viability and complete differentiation. Such reactors would also be useful for drug manufacture, drug metabolism, toxicology studies, and complex biological studies.

Another potential use for HBM media of the present invention is in autotransplantation of hepatocytes. Hepatocyte transplant is a relatively new approach to treating patients with endstage liver disease. The method relies on use of donor organs which are not used for organ transplant. Autotransplantation has the advantage of not requiring immunosuppressive drugs, but it is not practical if it is not possible to expand the number of cells and keep them alive long enough to place them back into the donor. Endstage liver explants could also provide a donor hepatocyte source under selected conditions, including encapsulation or genetic manipulation. Regardless of the source of hepatocytes, expansion of cell number in long term culture and replantation (into spleen, portal system, peritonium, renal capsule, etc.), does enhance effective hepatic synthetic and detoxification processes for prolonged periods of time. The limiting point is the lack of hepatocytes. HBM has the potential to eliminate this lack of cells, and thereby dramatically expand the number of patients that could be treated for liver failure. Similarly, autotransplantation or heterotransplantation with other cells grown in the media of the present invention could expand the number of patients and array of treatments possible with biocellular therapies.

The HBM of the present invention can also be useful for drug and chemical testing procedures. Virtually all drugs, chemicals, and other manufactured products must be tested for mutagenicity and toxicity in hepatocyte cultures as part of FDA, USDA, NIOSH and EPA regulations. Currently, these tests are performed on rat hepatocytes in short term culture because of lack of long term viability or significant proliferation. The use of HBM will (1) extend the testing period (longer term viability), (2) allow longer exposure periods at lower concentrations, (3) allow observation of mutagenicity and toxicity on proliferating hepatocytes, and (4) make available a supply of human hepatocytes which could be used in other toxicologic investigations.

Although the invention has been described in detail for the purpose of illustration, it is to be understood that such detail is solely for that purpose and that variations can be made therein by those skilled in the art without departing from the spirit and scope of the invention except as it may be limited by the claims.

I claim:

1. A cell culture medium that allows the expansion of hepatocytes in vitro without serum, said medium comprising a basal medium modified to include nicotinamide; transferrin chelated with iron; insulin or insulin-like growth factors; glucocorticoid steroid; trace metals; at least one carbohydrate selected from the group consisting of glucose and galactose; arginine; proline; and glutamine in the culture medium in amounts effective to increase the total number of viable hepatocytes in the culture medium above the total number of viable hepatocytes introduced into the culture medium which allows expansion of hepatacytes in vitro without serum.

2. The cell culture medium of claim 1 comprising 1–150 mg/L arginine; 1–120 mg/L proline; 1–3050 mg/L nicotinamide; 0.1–100 mg/L transferrin chelated with iron; greater than $10^{-11}$M insulin or insulin-like growth factors; $10^{12}$M–$10^{-3}$M glucocorticoid steroid; 1–6000 µg/L zinc salt; 1–250 µg/L manganese salt; 1–1000 µg/L copper salt; 1–150 µg/L selenium salt; 2.0–10.0 mM L-glutamine; 0.01–5.0 g/L D-galactose or 0.01–5.0 g/L D-glucose, or when both D-galactose and D-glucose are included together, 0.01–8.0 g/L.

3. The culture medium of claim 1 wherein said trace metals comprise zinc, manganese, copper, and selenium.

4. The culture medium of either of claims 3 or 2 wherein said trace metals further comprise $ZnCl_2$, $ZnSO_4$, $MnSO_4$, and $CuSO_4$.

5. The culture medium of either of claims 1 or 2 further comprising one or more of the following: Growth factors functioning as a mitogen for said cells; Albumin, Sodium Pyruvate; Gamma Tocopherol; Alpha Tocopherol; Vitamin $D_3$; Dextran; Linolenic Acid; Apo-transferrin and Iron Gluconate; Retinol; Vitamin $B_{12}$; Ascorbic acid; Choline Chloride; Biotin.

6. The culture medium of either of claims 1 or 2 further comprising one or more additional growth factors, said growth factor functioning as a mitogen for said cells.

7. The culture medium of claim 6 wherein said one or more additional growth factors is selected from the group consisting of hepatocyte growth factor, epidermal growth factor, and transforming growth factor alpha.

8. The culture medium of either of claims 1 or 2 further comprising one or more of the following: Growth factors functioning as a mitogen for said cells; Albumin, 0–10.0 g/L; Sodium Pyruvate, 0–2.0 g/L; Gamma Tocopherol, 0–3.5 mg/L; Alpha Tocopherol, 0–2.5 mg/L; Vitamin $D_3$, 0–1.8 mg/L; Dextran, 0–5.0 g/L; Linolenic Acid, 0–5.0 g/L; Apo-transferrin, 0–20.0 mg/L and Iron Gluconate, 0–100 μg/L; Retinol, 0–2.0 mg/L; Vitamin $B_{12}$, 0–2.0 mg/L; Ascorbic acid, 0–10.0 mg/L; Choline Chloride, 0.2–12.5 mg/L; Biotin, 0.2–15.0 mg/L.

9. The culture medium of either of claims 1 or 2 further including one or more of the following: growth factors functioning as a mitogen for said cells; Albumin, 2.0 g/L; Sodium Pyruvate, 0.15 g/L; Gamma Tocopherol, 0.35 mg/L; Alpha Tocopherol, 0.15 mg/L; Vitamin $D_3$, 0.20 mg/L; Dextran, 2.0 g/L; Linolenic Acid, 1.0 g/L; Apo-transferrin, 5.0 mg/L and Iron Gluconate, 25.0 μg/L; Retinol, 0.05 mg/L; Vitamin $B_{12}$, 0.15 mg/L; Ascorbic acid, 3.0 mg/L; Choline Chloride, 1.5 mg/L; Biotin, 0.75 mg/L.

10. The culture medium of either of claims 1 or 2 wherein said basal medium is selected from the group consisting of DMEMs, MEMs, Williams' Media E, Eagle's basal media, DMEMs/F-12s, Media 199, F-12 (Ham) Nutrient Mixtures, F-10 (Ham) Nutrient Mixtures, and RPMI Media.

11. The culture medium of claim 10 wherein said basal medium is DMEM.

12. The culture medium of claim 11 wherein said DMEM contains 2.0 g/L D-glucose.

13. The cell culture medium of either of claims 1 or 2 in which said glucocorticoid steroid is selected from the group consisting of cortisol, cortisol derivative such as prednisone, prednisilone, and hydrocortisone, and dexamethasone.

14. A mixture of components that when added to liquid form the cell culture medium of either of claims 1 or 2.

15. A cell culture medium that allows expansion of hepatocytes in vitro without serum comprising: $CaCl_2$ (anhyd.), 200.00 mg/L; $Fe(NO_3)_3.9H_2O$, 0.10 mg/L; KCl, 400 mg/L; $MgSO_4$ (anhyd.), 97.67 mg/L; NaCl, 6,400.00 mg/L; $NaHCO_3$, 3,700.00 mg/L; $NaH_2PO_4.H_2O$, 125.00 mg/L; L-cystine.2HCl, 63.00 mg/L; glycine, 30.00 mg/L; L-histidine.HCl.$H_2O$, 42.00 mg/L; L-isoleucine, 105.00 mg/L; L-leucine, 105.00 mg/L; L-lysine.HCl, 146.00 mg/L; L-methionine, 30.00 mg/L; L-phenylalanine, 66.00 mg/L; L-serine, 42.00 mg/L; L-threonine, 95.00 mg/L; L-tryptophan, 16.00 mg/L; L-tyrosine.2Na.$2H_2O$, 104.00 mg/L; L-valine, 94.00 mg/L; D-Ca pantothenate, 4.00 mg/L; choline chloride, 4.00 mg/L; folic acid, 4.00 mg/L; i-inositol, 7.20 mg/L; pyridoxine HCl, 178 mg/L; pyridoxal HCl, 222 mg/L; riboflavin, 0.40 mg/L; thiamine.HCl, 4.00 mg/L; D-galactose, 0.01–5.0 g/L, D-glucose, 0.01–5.0 g/L, or when both are used, then 0.01–8.0 g/L; nicotinamide, 1–3050 mg/L; L-proline, 1–120 mg/L; L-arginine, 1–150 mg/L; L-ornithine, 1–500 mg/L; holo-transferrin, 0.1–100 mg/L; insulin, greater than $10^{-11}$M; dexamethasone, $10^{-12}$M–$10^{-3}$M; $ZnCl_2$, 1–3000 μg/L; $MnSO_4$, 1–250 μg/L; $ZnSO_4.7H_2O$, 1–3000 μg/L; $CuSO_4.5H_2O$, 1–1000 μg/L; selenium, 1–150 μg/L; L-glutamine, 2.0–10.0 mM; HEPES, 5–50 mM.

16. A cell culture medium that allows expansion of hepatocytes in vitro without serum comprising: $CaCl_2$ (anhyd.), 200.00 mg/L; $Fe(NO_3)_3.9H_2O$, 0.10 mg/L; KCl, 400 mg/L; $MgSO_4$ (anhyd.), 97.67 mg/L; NaCl, 6,400.00 mg/L; $NaHCO_3$, 3,700.00 mg/L; $NaH_2PO_4.H_2O$, 125.00 mg/L; L-cystine.2HCl, 63.00 mg/L; glycine, 30.00 mg/L; L-histidine.HCl.$H_2O$, 42.00 mg/L; L-isoleucine, 105.00 mg/L; L-leucine, 105.00 mg/L; L-lysine.HCl, 146.00 mg/L; L-methionine, 30.00 mg/L; L-phenylalanine, 66.00 mg/L; L-serine, 42.00 mg/L; L-threonine, 95.00 mg/L; L-tryptophan, 16.00 mg/L; L-tyrosine.2Na.$2H_2O$, 104.00 mg/L; L-valine, 94.00 mg/L; D-Ca pantothenate, 4.00 mg/L; choline chloride, 4.00 mg/L; folic acid, 4.00 mg/L; i-inositol, 7.20 mg/L; pyridoxine HCl, 178 mg/L; pyridoxal HCl, 222 mg/L; riboflavin, 0.40 mg/L; thiamine.HCl, 4.00 mg/L; D-galactose, 2.0 g/L, D-glucose, 2.0 g/L; nicotinamide, 610 mg/L; L-proline, 30 mg/L; L-arginine, 84 mg/L; L-ornithine, 100 mg/L; holo-transferrin, 5 mg/L; insulin, 5 mg/L; dexamethasone, $1 \times 10^{-7}$M; $ZnCl_2$, 0.544 mg/L; $MnSO_4$, 0.025 mg/L; $ZnSO_4.7H_2O$, 0.750 mg/L; $CuSO_4.5H_2O$, 0.20 mg/L; selenium, 5 μg/L; L-glutamine, 5.0 mM; HEPES, 20 mM.

17. The culture medium of claim 15 in which the following components are found in the specified amounts: purified bovine albumin, 2.0 g/L; D-glucose, 2.0 g/L; D-galactose 2.0 g/L, L-ornithine 0.1 g/L, L-proline, 0.030 g/L, nicotinamide, 0.610 g/L, $ZnCl_2$, 0.544 mg/L, $ZnSO_4.7H_2O$, 0.750 mg/L, $CuSO_4.5H_2O$, 0.20 mg/L, $MnSO_4$, 0.025 mg/L, glutamine, 5.0 mM, ITS (rh-insulin) 5.0 mg/L; human transferrin, 5.0 mg/L (30% diferric iron saturated), selenium, 5.0 μg/L; dexamethasone, $10^{-7}$M; and HEPES buffer, 20.0 mM.

18. The culture medium of either of claims 15 or 16 further including one or more of the following: growth factor functioning as a mitogen for said cells; Albumin, 2.0 g/L; Sodium Pyruvate, 0.15 g/L; Gamma Tocopherol, 0.35 mg/L; Alpha Tocopherol, 0.15 mg/L; Vitamin $D_3$, 0.20 mg/L; Dextran, 2.0 g/L; Linolenic Acid, 1.0 g/L; Apo-transferrin, 5.0 mg/L and Iron Gluconate, 25.0 μg/L; Retinol, 0.05 mg/L; Vitamin $B_{12}$, 0.15 mg/L; Ascorbic acid, 3.0 mg/L; Choline Chloride, 1.5 mg/L; Biotin, 0.75 mg/L.

19. The culture medium of either of claims 15 or 16 further comprising one or more of the following: Growth factors functioning as a mitogen for said cells; Albumin, 0–10.0 g/L; Sodium Pyruvate, 0–2.0 g/L; Gamma Tocopherol, 0–3.5 mg/L; Alpha Tocopherol, 0–2.5 mg/L; Vitamin $D_3$, 0–1.8 mg/L; Dextran, 0–5.0 g/L; Linolenic Acid, 0–5.0 g/L; Apo-transferrin, 0–20.0 mg/L and Iron Gluconate, 0–100 μg/L; Retinol, 0–2.0 mg/L; Vitamin $B_{12}$, 0–2.0 mg/L; Ascorbic acid, 0–10.0 mg/L; Choline Chloride, 0.2–12.5 mg/L; Biotin, 0.2–15.0 mg/L.

* * * * *